(12) United States Patent
Chanduszko et al.

(10) Patent No.: US 9,486,304 B2
(45) Date of Patent: Nov. 8, 2016

(54) TUBULAR FILTER

(71) Applicant: C. R. Bard, Inc., Murray Hill, NJ (US)

(72) Inventors: Andrzej J. Chanduszko, Chandler, AZ (US); Michael A. Randall, Gilbert, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 14/697,489

(22) Filed: Apr. 27, 2015

(65) Prior Publication Data

US 2015/0238302 A1 Aug. 27, 2015

Related U.S. Application Data

(60) Division of application No. 14/107,289, filed on Dec. 16, 2013, now Pat. No. 9,017,367, which is a division of application No. 12/846,680, filed on Jul. 29, 2010, now Pat. No. 8,613,754, which is a continuation-in-part of application No. 11/429,975, filed on May 9, 2006, now Pat. No. 7,967,838.

(60) Provisional application No. 61/229,580, filed on Jul. 29, 2009, provisional application No. 60/680,601, filed on May 12, 2005.

(51) Int. Cl.
*A61F 2/01* (2006.01)

(52) U.S. Cl.
CPC ............ *A61F 2/01* (2013.01); *A61F 2002/011* (2013.01); *A61F 2002/016* (2013.01); *A61F 2002/018* (2013.01); *A61F 2220/0016* (2013.01); *A61F 2230/005* (2013.01); *A61F 2230/008* (2013.01); *A61F 2230/0067* (2013.01); *A61F 2250/0037* (2013.01)

(58) Field of Classification Search
CPC ............... A61F 2/01; A61F 2002/018; A61F 2220/0016; A61F 2230/008; A61F 2002/016; A61F 2230/005; C61F 2002/011
USPC ........................................................ 606/200
See application file for complete search history.

(56) References Cited

U.S. PATENT DOCUMENTS 6,231,589 B1 * 5/2001 Wessman .................. A61F 2/01
 606/200
2004/0186510 A1 * 9/2004 Weaver ..................... A61F 2/01
 606/200

* cited by examiner

*Primary Examiner* — Vy Bui
(74) *Attorney, Agent, or Firm* — C.R. Bard Intellectual Property; Buchalter Nemer

(57) ABSTRACT

A method of preparing a filter for delivery into a body vessel. The filter includes a hub disposed along a longitudinal axis and a plurality of anchor members extending from the hub. Each anchor member includes either a cranial extension or a caudal extension at a distal end thereof. At least one anchor member distal end may be spaced from the hub at each of a first, second, and third distance along the longitudinal axis. The filter also includes a plurality of locator members extending from the hub, the locator members alternatingly interposed between the anchor members.

13 Claims, 24 Drawing Sheets

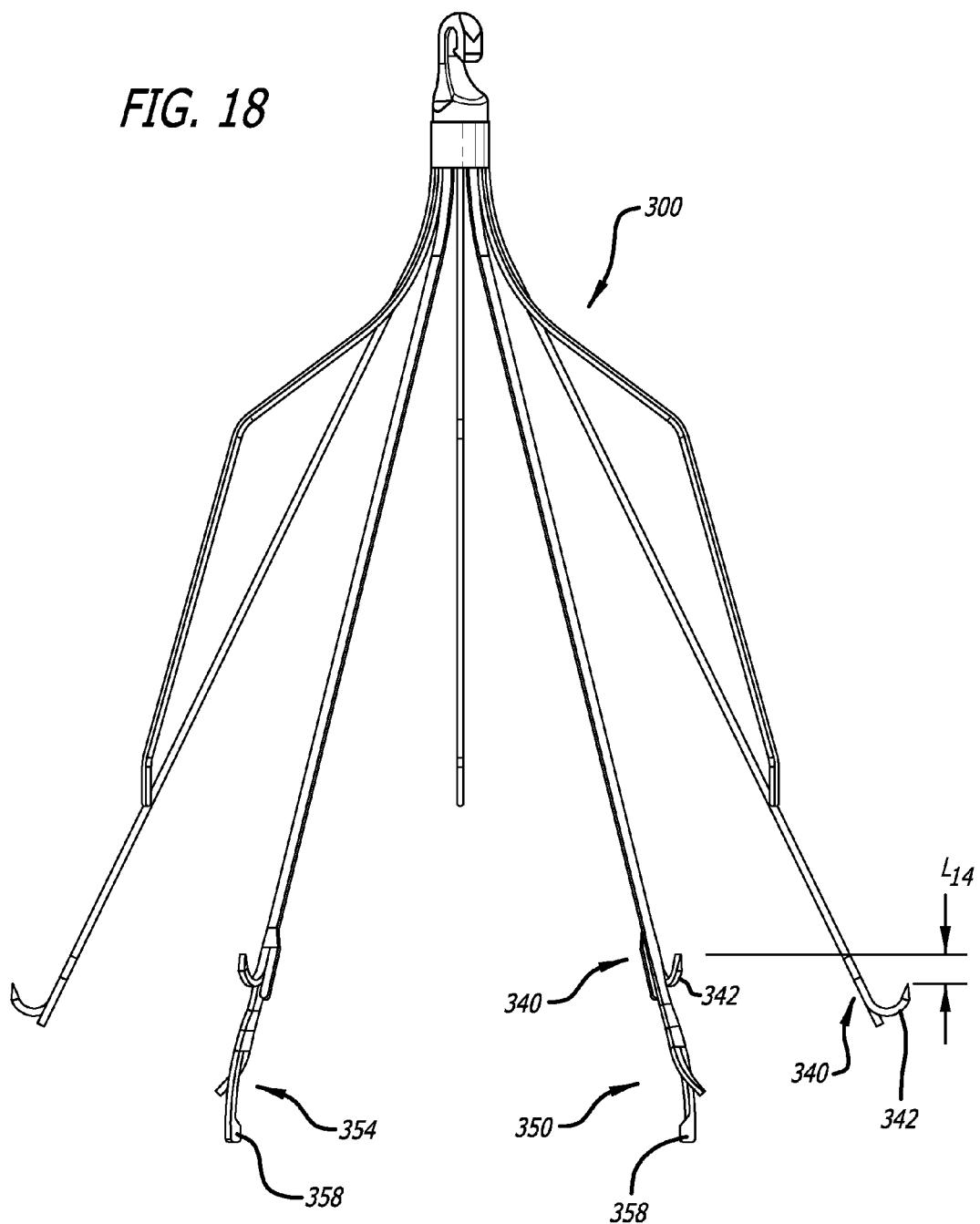

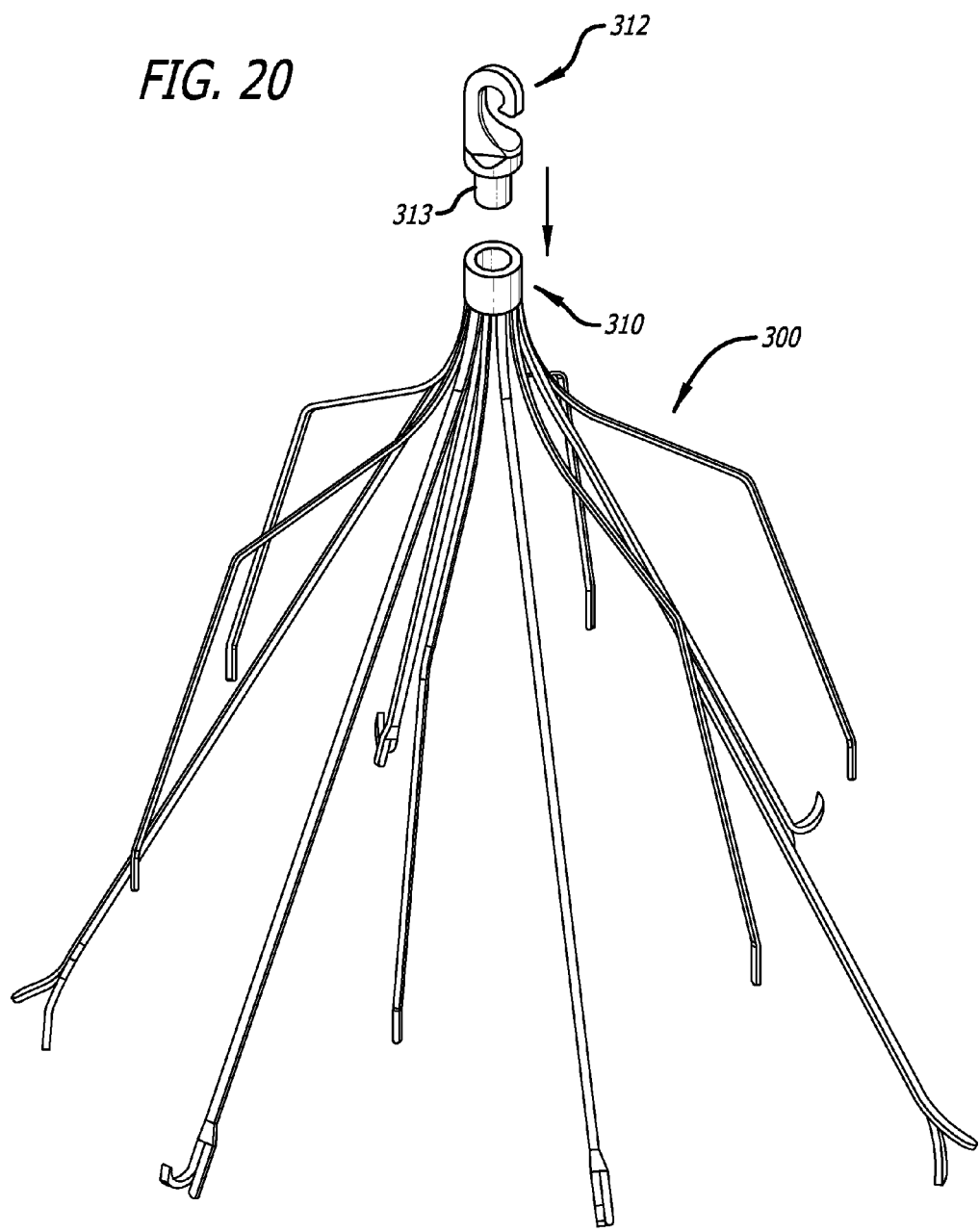

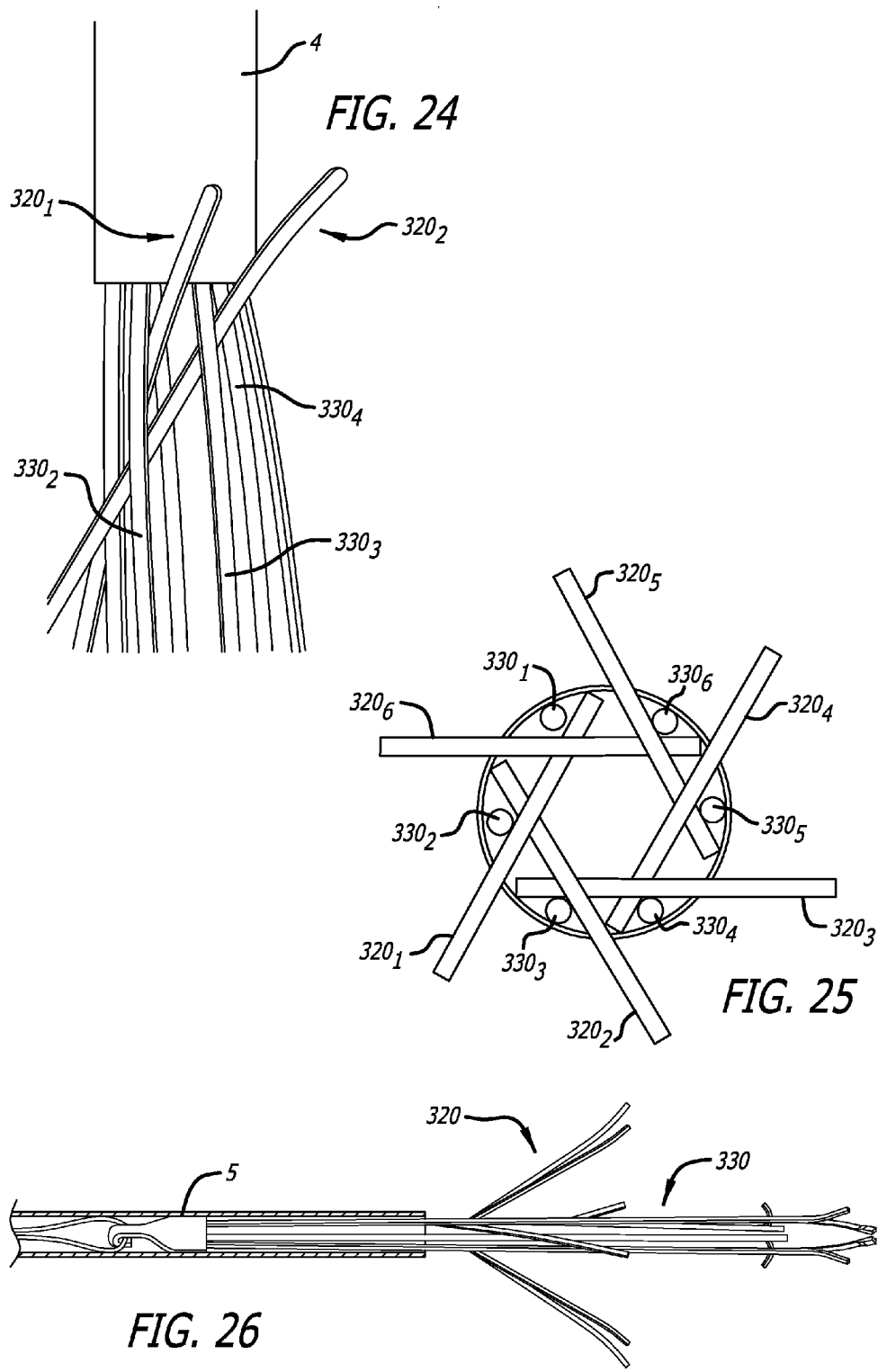

TUBULAR FILTER

PRIORITY

This application is a division of U.S. application Ser. No. 14/107,289, filed Dec. 16, 2013, now U.S. Pat. No. 9,017,367, which is a division of U.S. application Ser. No. 12/846,680, filed Jul. 29, 2010, now U.S. Pat. No. 8,613,754, which claims the benefit of priority to U.S. Provisional Patent Application No. 61/229,580, filed Jul. 29, 2009, and is a continuation-in-part of U.S. patent application Ser. No. 11/429,975, filed May 9, 2006, now U.S. Pat. No. 7,967,838, which claims the benefit of priority to U.S. Provisional Patent Application No. 60/680,601, filed May 12, 2005. Each of the aforementioned applications is incorporated by reference in its entirety into this application.

BACKGROUND

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein, such as the vena cava. These vena cava filters are designed to remain in place permanently. Such filters include structure to anchor the filter in place within the vena cava, such as elongate diverging anchor members with hooked ends that penetrate the vessel wall and positively prevent migration in either direction longitudinally of the vessel. The hooks on filters of this type are rigid and will not bend, and within two to six weeks after a filter of this type has been implanted, the endothelium layer grows over the diverging anchor members and positively locks the hooks in place. Now any attempt to remove the filter results in a risk of injury to or rupture of the vena cava.

A number of conditions and medical procedures subject the patient to a short term risk of pulmonary embolism which can be alleviated by a filter implant. In such cases, patients are often averse to receiving a permanent implant, for the risk of pulmonary embolism may disappear after a period of several weeks or months. However, most existing filters are not easily or safely removable after they have remained in place for more than several weeks, and consequently longer-term temporary filters that do not result in the likelihood of injury to the vessel wall upon removal are not available.

In an attempt to provide a removable filter, two filter baskets have been formed along a central shaft that are conical in configuration, with each basket being formed by spaced struts radiating outwardly from a central hub for the basket. The central hubs are held apart by a compression unit, and the locator members of the two baskets overlap so that the baskets face one another. Filters of this type require the use of two removal devices inserted at each end of the filter to draw the baskets apart and fracture the compression unit. The end sections of the locator members are formed to lie in substantially parallel relationship to the vessel wall and the tips are inclined inwardly to preclude vessel wall penetration. If a device of this type is withdrawn before the endothelium layer grows over the locator members, vessel wall damage is minimized. However, after growth of the endothelium layer the combined inward and longitudinal movement of the filter sections as they are drawn apart can tear this layer.

Each of the following patents and published patent applications relate to IVC or blood filters and is incorporated by reference in its entirety into this application: U.S. Pat. Nos. 5,059,205; 6,007,558; 6,273,901; 6,287,332; 6,589,266; 7,338,512; 7,544,202; 7,625,390; US Publication No. 2007/0167974; US Publication No. 2007/0198050; US Publication No. 2008/0039891; WO 1999/025252; WO 2002/0004060; WO 2004/098459; WO 2004/098460; WO 2005/072645; WO 20051102437; WO 20051102439; WO 2006/036457; WO 20061124405; WO 20071100619; and WO 20071106378.

BRIEF SUMMARY

The various embodiments provide for a removable blood filter that allows for filtering of an embolus in a blood vessel by utilizing a plurality of locators and a plurality of anchors. In one aspect, a filter to be placed in a flow of blood through a vessel includes a hub, at least one anchor, and at least one locator. The hub can be disposed along a longitudinal axis. The at least one anchor projects from the hub and includes a hook that penetrates a wall of the blood vessel when the filter is placed in the blood vessel. The hook can be spaced along the longitudinal axis from the hub and spaced a first radial distance from longitudinal axis. The at least one locator has a tip or portion of the locator that engages the wall of the vessel. The tip can be spaced along the longitudinal axis from the hub and spaced a second radial distance from the longitudinal axis. The second radial distance can be less than the first radial distance. The at least one locator has at least four portions and each of the portions can be disposed on respective distinct axes.

In yet another aspect, the various embodiments also provides for a filter to be placed in a flow of blood through a vessel. The filter includes a hub, at least one anchor, and at least one locator. The hub can be disposed along a longitudinal axis. The at least one anchor projects from the hub and includes a hook that penetrates a wall of the blood vessel when the filter is placed in the blood vessel. The hook can be spaced along the longitudinal axis from the hub and spaced a first radial distance from the longitudinal axis. The at least one locator projects from the hub and has a tip or portion of the locator that engages the wall of the vessel. The tip can be spaced along the longitudinal axis from the hub and spaced a second radial distance from the longitudinal axis where the second radial distance can be less than the first radial distance. The locator can be disposed proximate the hub and has at least four portions, and each of the at least four portions can be disposed on respective distinct axes. The at least four portions can include a curved portion being disposed on a radius of curvature that extends along the longitudinal axis.

In yet a further aspect of the various embodiments, a filter is provided to be placed in a flow of blood through a vessel. The filter includes a hub, at least one anchor and at least one locator. The hub can be disposed along a longitudinal axis. The at least one anchor projects from the hub and includes a hook that penetrates a wall of the blood vessel when the filter is placed in the blood vessel, spaced along the longitudinal axis from the hub, and spaced a first radial distance from longitudinal axis. The at least one locator projects from the hub and has a tip or portion of the locator that engages the wall of the vessel. The tip can be spaced along the longitudinal axis from the hub, and spaced a second radial distance from the longitudinal axis, where the second radial distance can be less than the first radial distance. The locator has a first portion distal to the hub and a second portion proximal to the hub. Each of the first and second portions can be generally linear and disposed on distinct axes oblique with respect to the longitudinal axis, where the length of the first portion can be greater than a length of the second portion.

In yet an additional aspect of the various embodiments, a filter is provided to be placed in a flow of blood through a vessel. The filter includes a hub, at least one anchor and at least one locator. The hub can be disposed along a longitudinal axis. The at least one anchor projects from the hub and includes a hook that penetrates a wall of the blood vessel, spaced along the longitudinal axis from the hub, and spaced a first radial distance from the longitudinal axis. The at least one locator projects from the hub and has a tip or portion of the locator that engages the wall of the vessel. The tip can be spaced along the longitudinal axis from the hub, and spaced a second radial distance from the longitudinal axis, where the second radial distance can be less than the first radial distance. The locator has first and second portions oblique to the longitudinal axis. The first portion can be distal to the hub, and a second portion can be proximal to the hub, where a length of the first portion being greater than a length of the second portion.

In yet another aspect of the various embodiments, a filter is provided to be placed in a blood vessel that includes a blood vessel wall. The filter includes a hub, and a first and a second set of members. The hub can be disposed along a longitudinal axis. Each of the first set of members extends from the hub. Each of the first set of members includes a hook spaced along the longitudinal axis from the hub, each hook being spaced radially from the longitudinal axis a first distance. Each of the second set of members extends from the hub and includes a tip being spaced along the longitudinal axis from the hub. Each tip can be spaced radially from the longitudinal axis a second distance less than the first distance.

In yet a further aspect of the various embodiments, a filter to be placed in a blood vessel is provided. The filter includes a hub, a plurality of anchors and a plurality of locators. The hub can be disposed along a longitudinal axis. The plurality of anchors branches from the hub. Each anchor includes a hook that: (i) penetrates a wall of the blood vessel, (ii) can be spaced along the longitudinal axis from the hub, and (iii) can be radially spaced from the longitudinal axis a first distance. The plurality of locators branches from the hub. Each locator includes a base portion proximate the hub, a first portion that extends from the base portion and along a first axis, a second portion that extends from the first portion and along a second axis, which can be distinct from the first axis, and a tip portion that extends from the second portion and along a tip axis, which can be distinct from the first and second axes. The tip portion (i) engages the wall of the blood vessel, (ii) can be spaced along the longitudinal axis from the hub, and (iii) can be radially spaced from the longitudinal axis a second distance, which can be less than the first radial distance.

In yet a further aspect of the various embodiments, a filter to be placed in a blood vessel is provided. The filter includes a hub, a plurality of anchors and a plurality of locators. The hub can be disposed along a longitudinal axis. The plurality of anchors branches from the hub. Each anchor includes a hook that: (i) penetrates a wall of the blood vessel, (ii) can be spaced along the longitudinal axis from the hub, and (iii) can be radially spaced from the longitudinal axis a first distance. The plurality of locators branches from the hub. Each locator includes a base portion proximate the hub, a tip portion that (i) can engage the wall of the blood vessel, (ii) can be spaced along the longitudinal axis from the hub, and (iii) can be radially spaced from the longitudinal axis a second distance, which can be less than the first radial distance, and an intermediate portion coupling the base and tip portion. The intermediate portion can include a first linear segment extending from the base portion a first length along a first axis, which can be oblique with respect to the longitudinal axis and a second linear segment extending between the tip portion and first portions a second length, which can be greater than the first length, and along a second axis, which can be oblique respect to the longitudinal axis and can be distinct from the first axis.

In yet another aspect of the various embodiments, a filter is provided. The filter is to be placed in a flow of blood contained by a wall of a blood vessel. The filter includes a hub that extends along a longitudinal axis and at least one first member having first and second generally linear segments. The filter also includes at least one second member having third and fourth generally linear segments. The first segment defines a portion of a first cone when the first segment is rotated about the longitudinal axis. The second segment defines a cylinder when the second segment is rotated about the longitudinal axis. The third and fourth segments define respective portions of a third and fourth cones when each of the segments is rotated about the longitudinal axis. At least one of the third and fourth segments has a hook portion that penetrates the wall of a blood vessel.

In yet a further aspect of the various embodiments, a blood filter is provided to be placed in a flow of blood contained by a wall of a blood vessel. The filter includes a hub, at least one anchor and a plurality of locators. The hub can be disposed along a longitudinal axis extending generally parallel to the flow of blood. The at least one anchor includes a hook that penetrates the wall of the vessel. The at least one anchor defines a generator of a first conical shape about a longitudinal axis. The first conical shape includes: (i) an apex disposed proximate the hub, each anchor (ii) can be spaced along the longitudinal axis from the hub, and (iii) can be radially spaced from the longitudinal axis at a first distance. The plurality of locators branches from the hub and defines a first frustum having a geometric centroid along the longitudinal axis.

In yet another aspect, a filter is provided. The filter can be placed in a flow of blood contained by a wall of a blood vessel. The filter includes a hub, a plurality of anchors, and a plurality of locators. The hub can be disposed along a longitudinal axis. The plurality of anchors branches from the hub. Each anchor can include a hook that (i) penetrates a wall of the blood vessel, (ii) can be spaced along the longitudinal axis from the hub, and (iii) can be radially spaced from the longitudinal axis a first distance. The plurality of locators branches from the hub. Each locator includes a base portion extending accurately from the hub. The base portion has a radius of curvature about a transverse axis located at a second distance generally radially from the longitudinal axis. Each of the locators has a tip contiguous to the wall of the vessel. A portion of the tip closest to the hub can be spaced at a third distance along the longitudinal axis from the hub and spaced a fourth radial distance from the longitudinal axis, the fourth radial distance being less than the third distance.

The various embodiments described above may further include a radio-opaque material on or as part of the filter hub. Also, the various embodiments described above may further include a bio-active agent incorporated with or as part of the filter.

The various embodiments further provide a method of centering a blood filtering device within a blood vessel having a plurality of locators extending from a hub to define a first volume and a plurality of anchors extending from the hub to define a second volume. The method can be achieved by enclosing more than 15 percent of the second volume in the first volume, and engaging a hook provided on each locator onto a wall of the blood vessel.

The various embodiments also provide for a blood filter with different types and configurations of hooks and anchors at different longitudinal positions along a filter longitudinal axis in order to address potential problems with insufficient anchoring and subsequent caudal or cranial movement. In one aspect, the various embodiments provide the blood filter with penetration limiters associated with the filter anchors and hooks to limit penetration through the vessel wall. In one aspect, the various embodiments also provide for a blood vessel filter that is formed by laser cutting a metal tube. In one embodiment, a filter to be placed in a flow of blood through a vessel, comprises a hub disposed along a longitudinal axis, a plurality of anchor members extending from the hub, each anchor member including either a cranial extension or a caudal extension at a distal end thereof, at least one anchor member distal end spaced from the hub at each of a first, second, and third distance along the longitudinal axis, and a plurality of locator members, each locator member extending from the hub between an adjacent pair of anchor members.

The various embodiments further provide for a method of preparing a blood filter for insertion into a body vessel, including folding/positioning the filter in a compact, small profile in order to provide space for filter hooks and anchors to reside, and also in order to prevent filter hooks and anchors from interfering with loading and/or delivery of the blood filter.

In one embodiment, a method of preparing the filter for delivery into a body vessel, the filter having six anchor members comprising first, second, third, fourth, fifth, and sixth anchor members arranged successively counterclockwise about a circumference of the hub when viewed from the anchor member distal ends, the filter further having six locator members comprising first, second, third, fourth, fifth, and sixth locator members arranged successively counterclockwise about a circumference of the hub when viewed from the anchor member distal ends, includes: (i) constraining the anchor members in a collapsed configuration; (ii) positioning a length of the first locator member closest clockwise of the first anchor member behind the first anchor member and the second anchor member such that a distal end of the first locator member extends between the second anchor member and the third anchor member; (iii) positioning a length of the second locator member behind the second anchor member and the third anchor member such that a distal end of the second locator member extends between the third anchor member and the fourth anchor member; (iv) positioning a length of the third locator member behind the third anchor member and the fourth anchor member such that a distal end of the third locator member extends between the fourth anchor member and the fifth anchor member; (v) positioning a length of the fourth locator member behind the fourth anchor member and the fifth anchor member such that a distal end of the fourth locator member extends between the fifth anchor member and the sixth anchor member; (vi) positioning a length of the fifth locator member behind the fifth anchor member and the sixth anchor member such that a distal end of the fifth locator member extends between the sixth anchor member and the first anchor member; (vii) positioning a length of the sixth locator member behind the sixth anchor member and the first anchor member such that a distal end of the sixth locator member extends between the first anchor member and the second anchor member; (viii) verifying that the anchor members with caudal extensions are surrounded by the anchor members with cranial extensions; and (ix) pulling the filter into a delivery sheath.

In one embodiment, a method of preparing the filter for delivery into a body vessel, the filter comprising N anchor members extending distally from a hub, the anchor members arranged and numbered successively counterclockwise about a circumference of the hub when viewed from a filter distal end, each anchor member including either a cranial extension or a caudal extension at a distal end thereof, and N locator members extending distally from the hub, the locator members arranged and numbered successively counterclockwise about a circumference of the hub when viewed from the filter distal end, each locator member extending from the hub between an adjacent pair of anchor members arranged such that locator member n is positioned immediately clockwise adjacent of anchor member n, wherein N is greater than 5, includes: (i) constraining the anchor members in a collapsed configuration; (ii) positioning a length of locator member 1 behind anchor member 1 and anchor member 2 such that a distal end of locator member 1 extends between anchor member 2 and anchor member 3; (iii) repeating step (ii) for locator members 2, 3, . . . , and N-2; (iv) positioning a length of locator member N-1 behind anchor member N-1 and anchor member N such that a distal end of locator member N-1 extends between anchor member N and anchor member 1; (v) positioning a length of locator member N behind anchor member N and anchor member 1 such that a distal end of locator member N extends between anchor member 1 and anchor member 2; (vi) verifying that the anchor members with caudal extensions are surrounded by the anchor members with cranial extensions; and (vii) pulling the filter into a delivery sheath.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

FIG. 18 is a different perspective view of the blood filter in FIG. 15.

FIG. 20 is a perspective view of one embodiment of a retrieval member for the blood filter in FIG. 15.

FIG. 24 is a close-up view of a portion of the blood filter of FIG. 15 at another stage of preparation for loading and delivery.

FIG. 25 is a schematic view of the filter from a distal end at another stage of preparation for loading and delivery.

FIG. 26 is a close-up view of a portion of the blood filter of FIG. 15 at another stage of preparation for loading and delivery.

DETAILED DESCRIPTION

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

Figure 1:
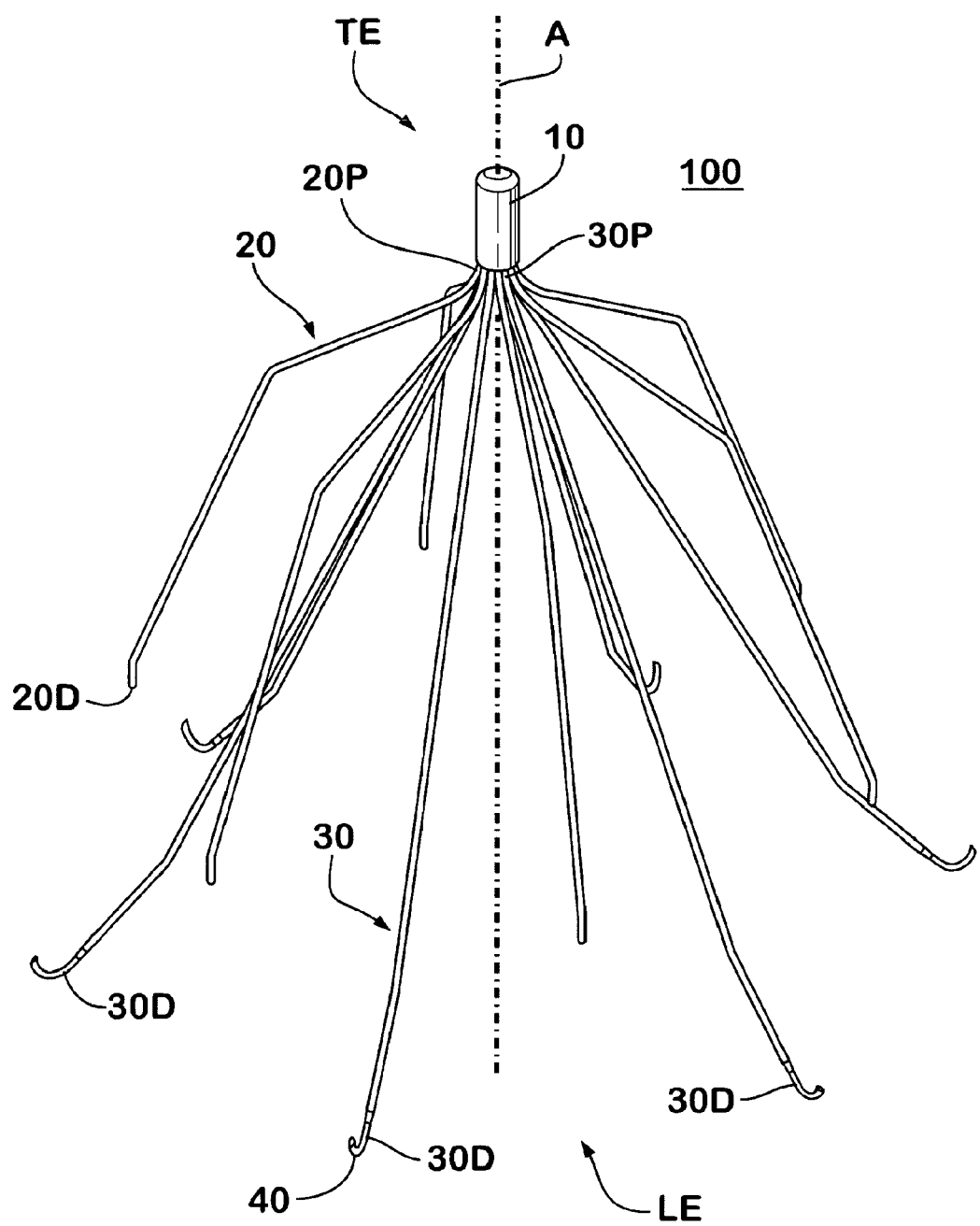
FIG. 1 is a top down perspective view of a preferred embodiment of the blood filter.
Figure 2:
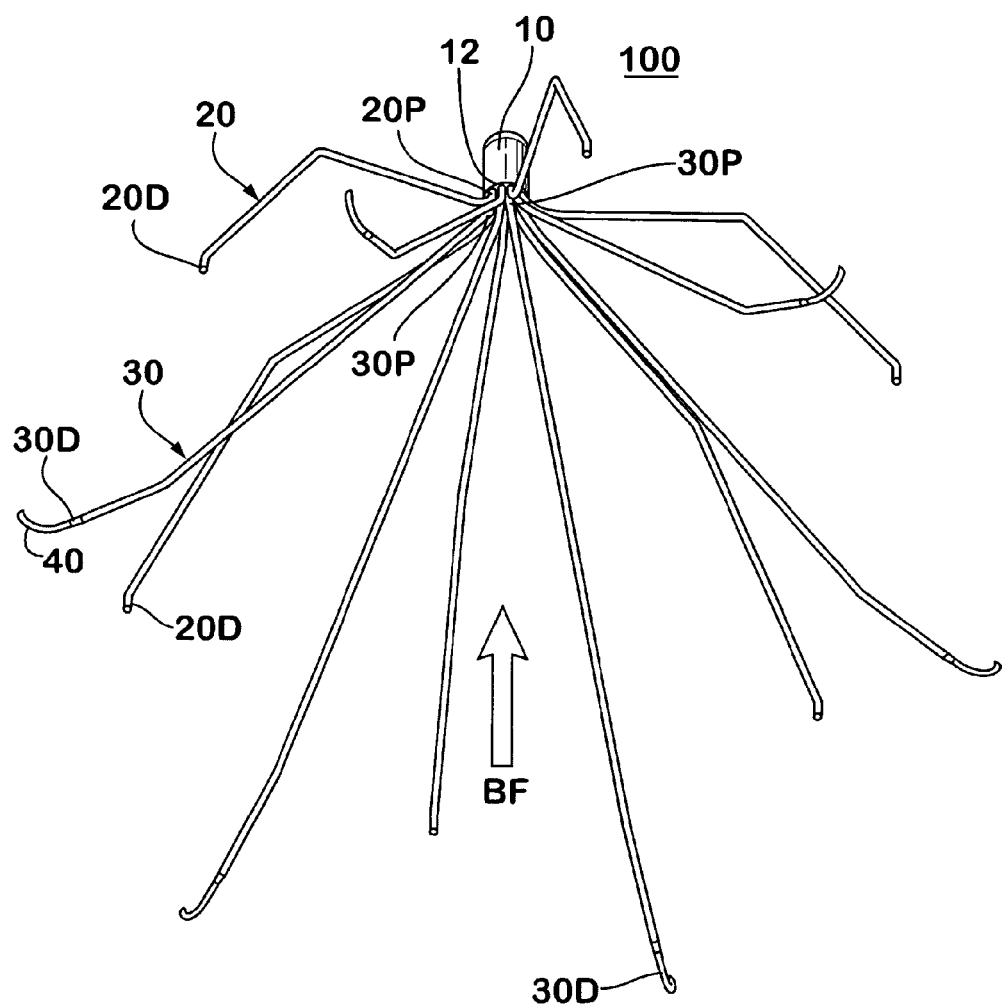
FIG. 2 is a bottom up perspective view of the embodiment of FIG. 1.

FIGS. 1-14 illustrate the preferred embodiments. Referring to FIG. 1, a filter 100 is illustrated in a perspective view. The filter 100 includes a hub 10, locator member 20, and anchor member 30 that has a hook 40. The filter 100 can be made from a plurality of elongate wires, which are preferably metal, such as, for example, Elgiloy, and more preferably are a super elastic shape memory alloy, such as Nitinol. The wires are held together at the filter trailing end by a hub 10 by a suitable connection technique, such as, for example, welding, laser welding, or plasma welding or being bonded together. Preferably, the wires are plasma welded. As used herein, "wire" refers to any elongated member of narrow cross section, including rods, bars, tubes, wire and narrow sections cut from thin plate, and is not intended to limit the scope of the invention to elongated members of circular cross section, cut from wire stock or manufacture according to a particular method of metal forming.

Figure 6:
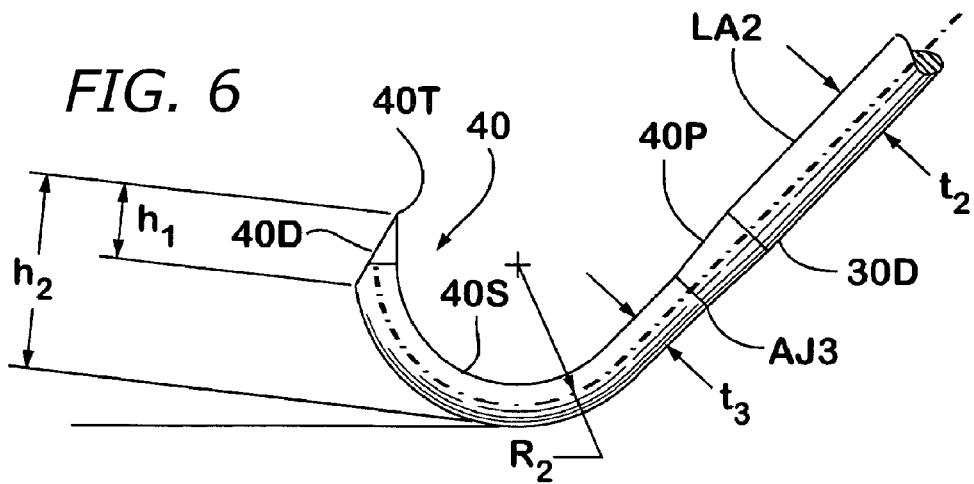
FIG. 6 is a close up side view of a hook of the anchor member for the filter of FIG. 1

The locator member 20 has a proximal locator end 20P and a distal locator end 20D. Similarly, the anchor member 30 has a proximal anchor end 30P and a distal anchor end 30D. The distal anchor end 30D can be provided, as shown in FIG. 6, with hook 40.

Figure 4A:
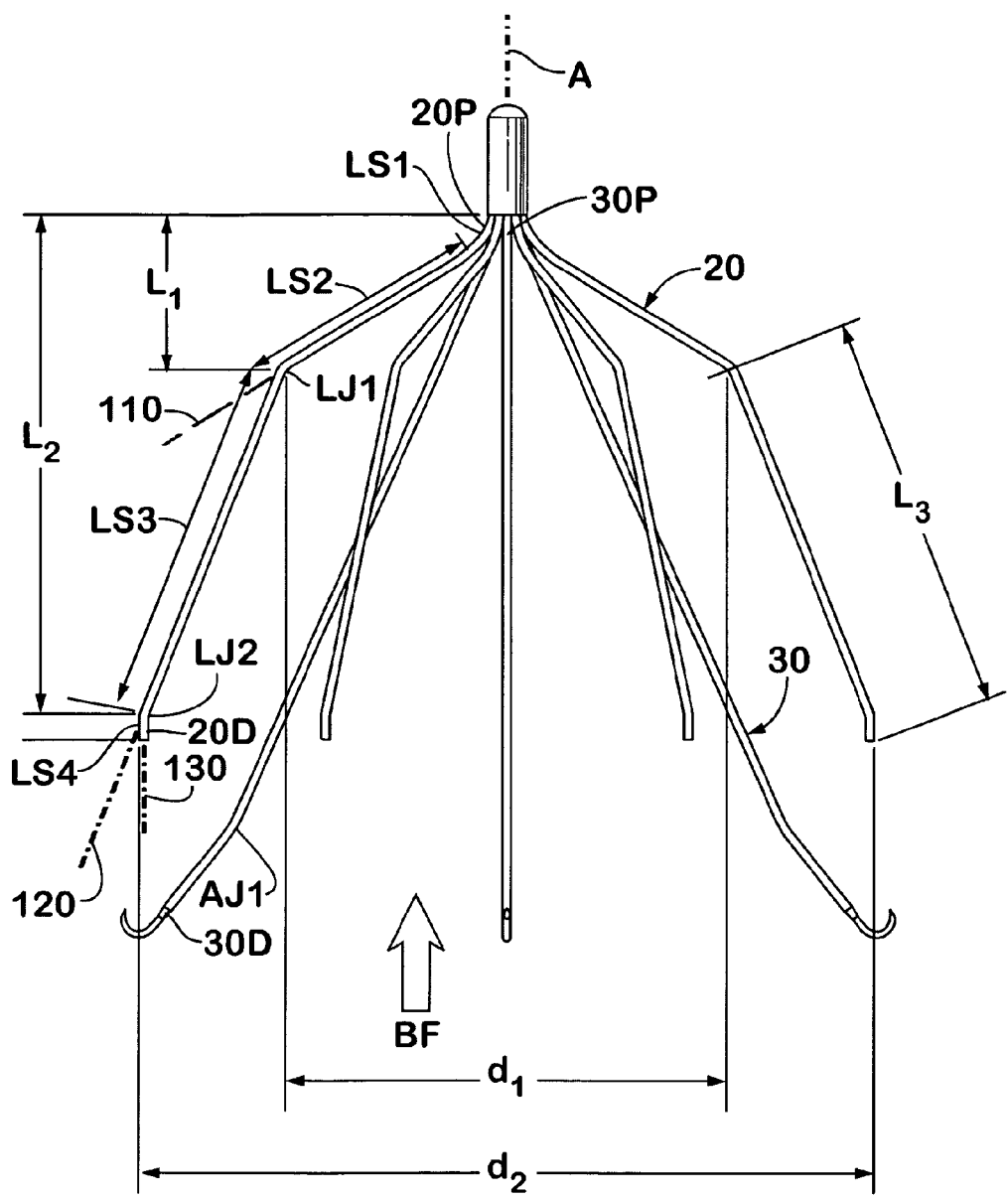
FIG. 4A is a side view of the filter viewed along view 4A-4A in FIG. 3.
Figure 4B:
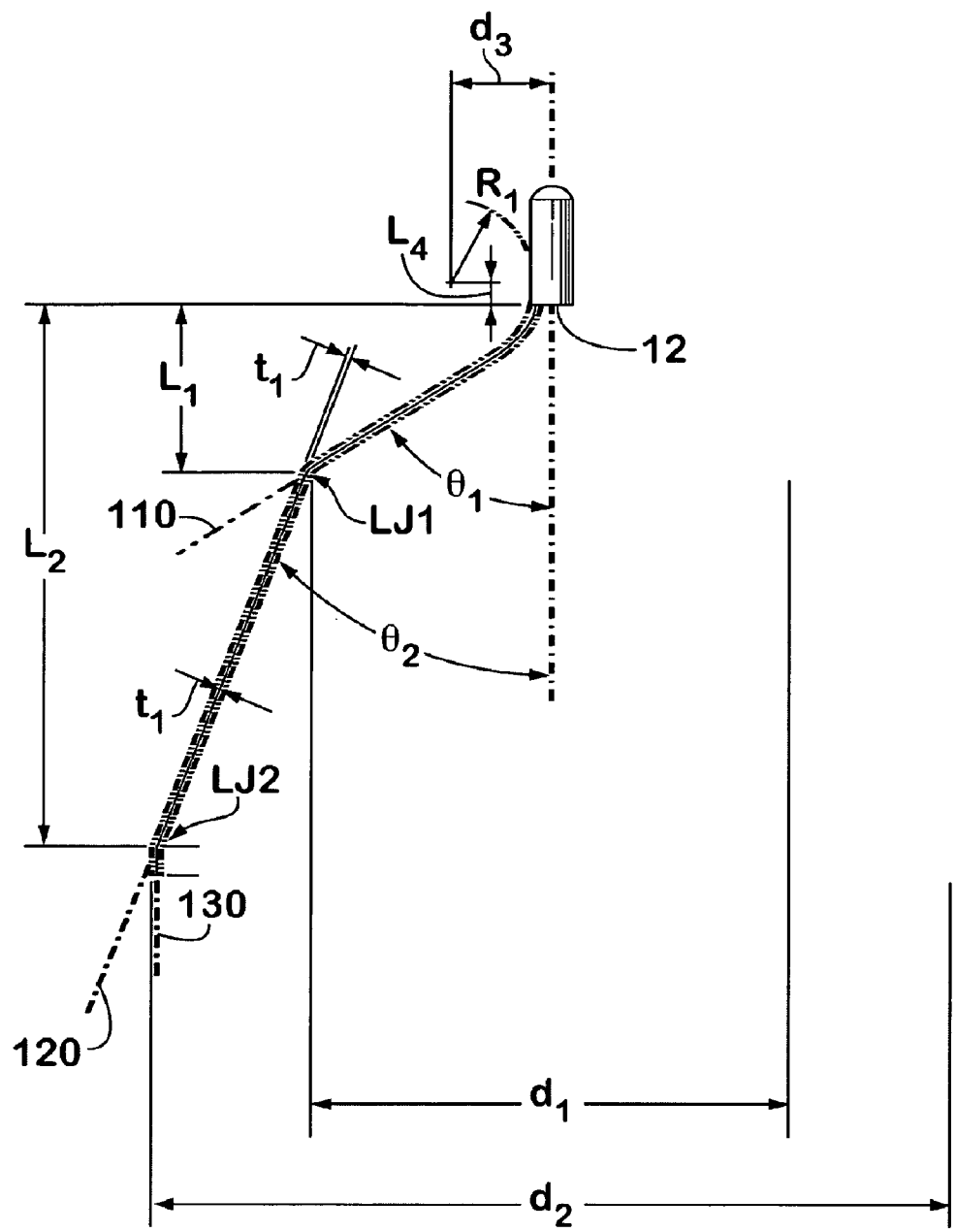
FIG. 4B is a side view of one arm or locator member of the filter of FIG. 1.

Referring to FIGS. 4A and 4B, the locator member 30 may be provided with a plurality of locator segments, preferably between 3 and 6 segments and more preferably four locator segments LSI, LS2, LS3, LS4. First locator segment LSI may be a curved portion extending away from the hub in a first direction along the longitudinal axis A. In an embodiment, the second locator segment LS2 extends generally linearly along a second axis 110; third locator segment LS3 extends generally linearly along a third axis 120; and the fourth locator segment LS4 extends generally linearly along a fourth axis 130. In a preferred embodiment, the various axes A, 110, 120, 130, and 140 are distinct from one another in that each may intersect with one another but none of them are substantially collinear with each other.

The locator segment LS2 may be distinct from locator segment LS3 by virtue of a joint or bend LJ1. The locator segment LS3 may be distinct from locator segment LS4 via a join or bend LJ2. The joint or bend LJ1 or LJ2 can be viewed as a location formed by the intersection of the segments defining a radiused portion connecting any two segments.

The locators 20 may range from 3 to 12 locators. The filter embodiment illustrated in FIG. 4A includes six locators that are generally equiangularly spaced about axis A. In the embodiment illustrated in FIG. 4B, locator segment LS1 extends through an arc with a radius of curvature $R_1$ whose center may be located along an axis orthogonal to axis A over a radially transverse distance $d_3$ and over a longitudinal distance $L_4$ as measured from a terminal surface 12 of the hub 10 along an axis generally parallel to the longitudinal axis A. The locator segment LS2 extends along axis 110 to form a first angle $\theta_1$ with respect to the longitudinal axis A whereas the locator segment LS3 extends along axis 120 to form second angle $\theta_2$. As shown in FIG. 4B, the first locator joint or bend LJ1 may be located at a longitudinal length L1 generally parallel to axis A from the terminal surface 12. The first locator joint or bend LJ1 may be also located at a distance of about one-half distance "$d_1$" from axis A on a generally orthogonal axis with respect to axis A as shown in FIG. 4A, where the distance $d_1$ is the distance between inside facing surfaces of respective diametrically disposed locators 20. The second locator joint LJ2 may be located over a longitudinal length $L_2$ generally parallel to axis A. The second locator join LJ2 may be located over a distance of about one-half diameter "$d_2$" from axis A. The distance $d_2$ is the distance between the outermost surface of the fourth segment LS4 of respective diametrically disposed locators 20. The thickness of locator member 20 is $t_1$. Where the locator member 20 is a wire of circular cross-section, the thickness $t_1$ of the locator 20 may be the diameter of the wire.

A range of values may be used for the aforementioned dimensional parameters in order to provide locator members that will locate the filter within the vein or vessel in which the filter is to be applied in a manner that positions segment LS4 approximately parallel to the walls of the vein or vessel and provides sufficient lateral force against the vein or vessel wall to center the filter but not so much force as to cause injury to the wall. For example, a filter intended to be placed in a narrow vein or vessel, such as a human infant or canine vena cava, may have smaller dimensions $L_1$, $L_2$, $L_3$, $L_4$, LSI, LS2, LS3, LS4, $d_1$ and $d_2$ so that the positioning members can deploy sufficiently to accomplish the positioning and filtering functions, than a filter intended to be placed in a large vein or vessel, such as an adult human vena cava or other vessel. In an example embodiment suitable for an adult human vena cava filter, when the filter is at the temperature of the subject and unconstrained, the radius of curvature $R_1$ is from about 0.02 inches to about 0.1 inches with the center of the radius $R_1$ being located over a distance $d_3$ from the axis A of about 0.1 inches and length $L_4$ of about 0.2 inches; the length $L_1$ is about 0.3 inches; length $L_2$ is about 0.9 inches; distance $d_1$ (as measured to the inside facing surfaces of diametrically disposed locators 20) is about 0.8 inches; distance $d_2$ is about 1.5 inches, the first angle $\theta_1$ is about 58 degrees, the second angle $\theta_2$ is about 22 degrees; and the thickness $t_1$ of the locator is about 0.013 inches. It should be noted that the values given herein are approximate, representing a dimension within a range of suitable dimensions for the particular embodiment illustrated in the figures, and that any suitable values can be used as long as the values allow the filter to function as intended in a blood vessel of a subject.

Figure 5A:
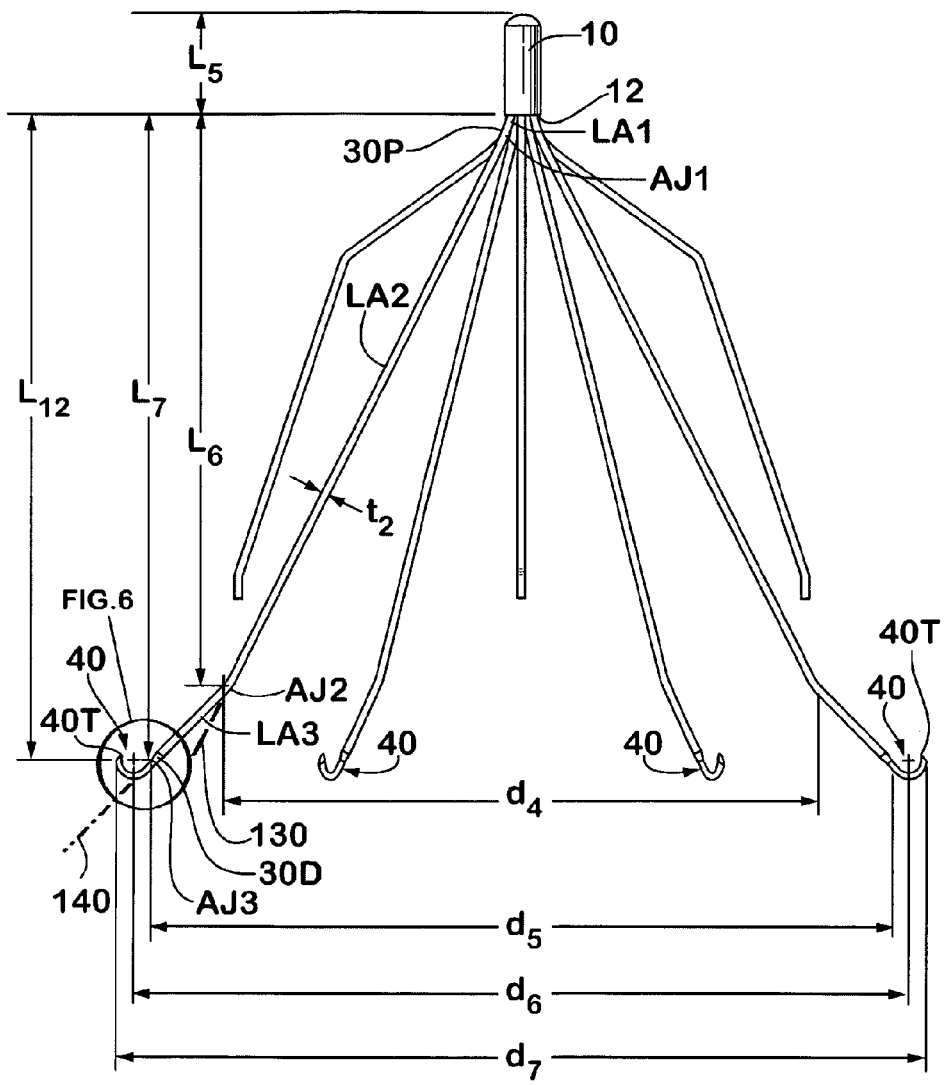
FIG. 5A is a side view of the filter viewed along view 5A-5A in FIG. 3.
Figure 5B:
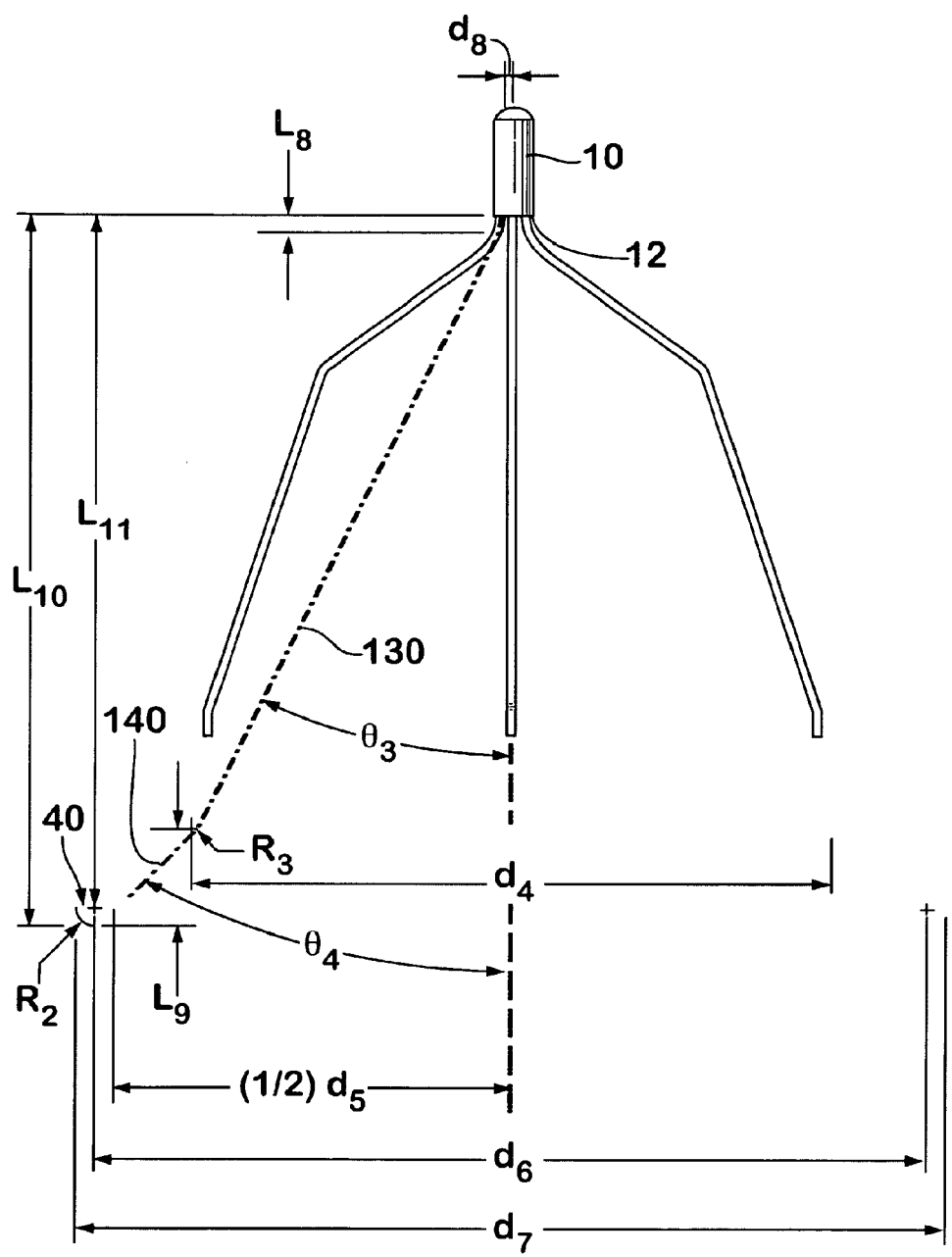
FIG. 5B is a side view of one locator member of the filter of FIG. 1.
Figure 5C:
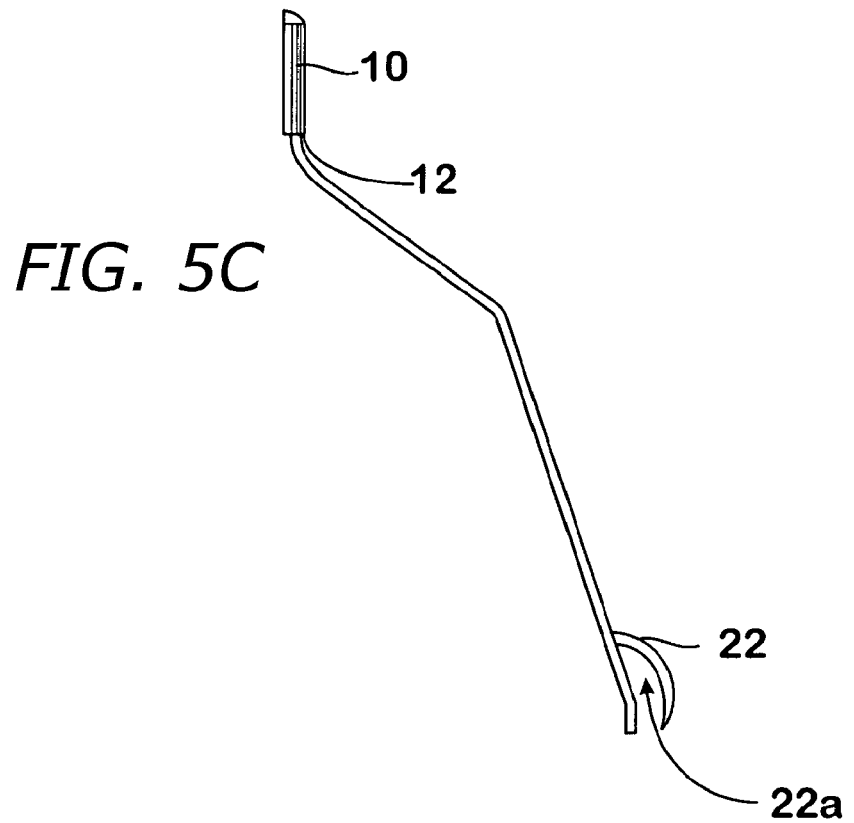
FIG. 5C is a side view of an alternative locator arrangement having a retention member disposed on the locator.

Referring to FIGS. 5A and 5B, the hub 10 can be provided with an internal cylindrical opening with a diameter of about two times the distance $d_8$. Each of the plurality of anchor members 30 can be provided with a first anchor segment LA1, a portion of which is disposed within the hub 10, connected to a second anchor segment LA2 by a first anchor joint or bend AJ1, which can be connected to a third anchor segment LA3 via a second anchor joint or bend AJ2. The third anchor segment LA3 can be connected to the hook 40 via third anchor joint or bend AJ3. The first anchor segment LA1 extends obliquely with respect to axis A. The second anchor segment LA2 extends along axis 130 oblique with respect to the axis A over an angle $\theta_3$ with respect to the longitudinal axis A. The third anchor segment LA3 extends along axis 140 oblique with respect to the longitudinal axis A over an angle $\theta_4$. The second anchor joint or bend AJ2 can be located at a sixth longitudinal distance $L_6$ as measured on an axis generally parallel to the axis A from the terminal surface 12 of the hub 10 and at about one half the fourth distance $d_4$ as measured between generally diametrical end points of two anchors 30 on an axis generally orthogonal to the axis A. The third anchor joint AJ3 can be located at a seventh longitudinal distance $L_7$ as measured along an axis generally parallel to axis A and at a transverse distance of about one-half distance $d_7$ as measured on an axis orthogonal to the axis A between the inner surfaces of two generally diametric anchors 30. The thickness of anchor member 30 is nominally $t_2$. Where the anchor member 30 is a wire of circular cross-section, the thickness $t_2$ of the anchor 30 may be the diameter of the wire. As shown in FIG. 5B, the hook 40 may be contiguous to a plane located at a longitudinal distance of $L_{11}$ as measured to the terminal surface 12 of hub 10. The hook 40 can be characterized by a radius of curvature $R_2$, in its expanded configuration at a suitable temperature, e.g., room temperature or the internal temperature of a subject. The center of the hook curvature $R_2$ can be located at a distance $L_{11}$ as measured along an axis generally parallel to the axis A from the terminal surface 12 of hub 10 and at one-half distance $d_6$ as measured between two generally diametrical hooks 40. The tips 40T of respective diametric hooks 40 may be located at longitudinal distance $L_{12}$ (which may be approximately the same as longitudinal distance $L_7$ to the third anchor joint AJ3) and at one half of distance $d_7$ between diametric hooks 40.

A range of values may be used for the aforementioned dimensional parameters in order to provide anchor members that will locate and anchor the filter within the vein or vessel in which the filter is to be applied in a manner that positions hooks 40 in contact with the walls of the vein or vessel and provides sufficient lateral force against the vein or vessel wall to ensure the hooks engage the wall but not so much force as to cause injury to the wall. For example, a filter intended to be placed in a narrow vein or vessel, such as a child or dog vena cava, may have smaller dimensions so that the anchor members can deploy sufficiently to accomplish the positioning, anchoring and filtering functions, than a filter intended to be placed in a large vein or vessels, such as an adult vena cava or other vessel. In an example embodiment suitable for an adult human vena cava filter, when the filter is at the temperature of the subject and unconstrained, the longitudinal distance $L_8$ is about 0.02 inches; $L_9$ is about 0.2 inches; $L_{10}$ is about 1.3 inches; $L_{11}$ is about 1.2 inches; $d_6$ is about 1.5 inches; $d_7$ is about 1.6 inches; $d_8$ is about 0.01 inches; $d_9$ is between 1.5 and 1.6 inches; $L_{12}$ is about 1.2 inches; the radius of curvature $R_2$ is about 0.03 inches; and the thickness $t_2$ of the anchor member is about 0.013 inches. Most preferably, a very small radius of curvature $R_3$ can characterize anchor joint or bend AJ2 where $R_3$ can be about 0.01 inches.

Figure 5D:
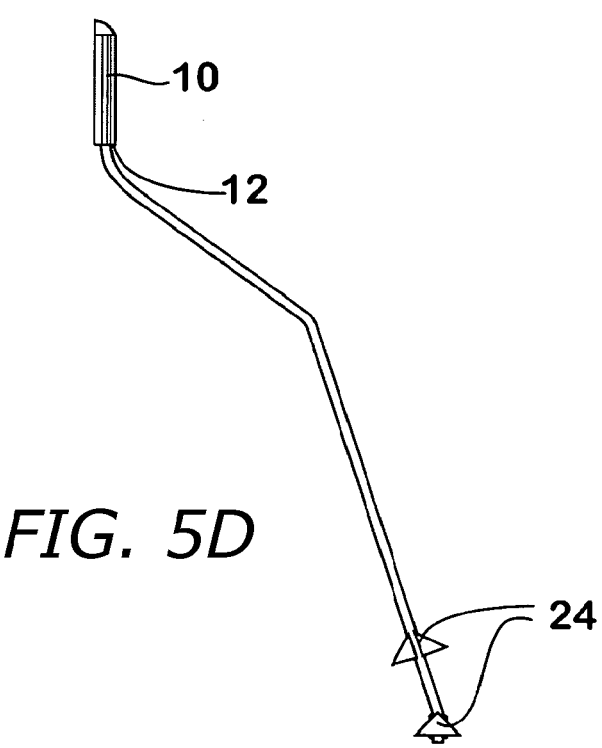
FIG. 5D is a side view of another locator arrangement having a support member to reduce or prevent penetration of a blood vessel wall by the locator.

In situation where additional retention of the filter may be desired, an anchor member can be coupled to the locator. One arrangement is shown exemplarily in FIG. 5C, where a hook 22 can be coupled to the locator proximate the tip portion. In this arrangement, both the tip portion and hook 22 are configured so that the locator does not penetrate through the blood vessel wall by formation of a stop region 22a defined by both the locator tip and the hook 22. Another arrangement can be by coupling or forming a hook in the same configuration as hook 40 for the anchor members. In yet another arrangement, shown here in FIG. 5D, where it may not be desirable to utilize a hook, one or more stop members 24 can be provided on the locator at any suitable locations. As shown in FIG. 5D, the stop member 24 is in the form of a truncated cone coupled to the locator. However, the stop member 24 can be of any configuration as long as the member 24 reduces or prevents penetration of the locator through the blood vessel wall. And in yet a further arrangement, the hook 22 (or hook 40) can be utilized in combination with the stop member 24 such as for example, a hook 22 coupled to a first locator, a hook 40 coupled to a second locator, a stop member 24 on a third locator, a combination of hook 22 and stop member 24 on a fourth locator, a combination of hook 40 and stop member 24 on a fifth locator.

Referring to FIG. 6, the hook 40 can be provided with a proximal hook portion 40P and a distal hook portion 40D on which a sharpened tip 40T is provided. The hook 40 can be formed to have a thickness $t_3$. Where the hook 40 is formed from a wire having a generally circular cross-section, the thickness $t_3$ may be generally equal to the outside diameter of the wire. In an embodiment, the hook thickness $t_3$ is approximately 0.5 to approximately 0.8 that of the anchor thickness $t_2$. The wire can be configured to follow a radius of curvature $R_2$ whose center is located at longitudinal distance $L_{11}$ and radial distance $d_9$ when the filter is at the temperature of a subject, as discussed above. The tip 40T can be provided with a generally planar surface 40D whose length can be approximately equal to length $h_1$. The tip 40T may be located over a distance $h_2$ from a plane tangential to the curved portion 40S.

Figure 7:
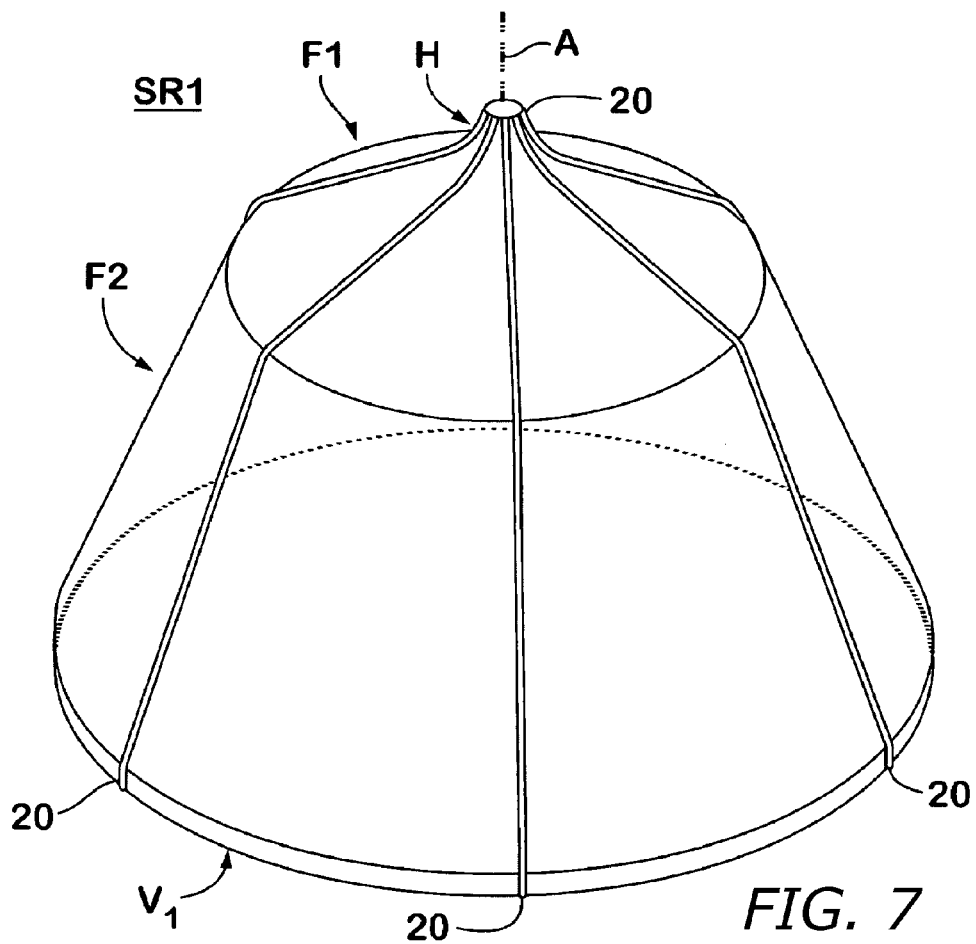
FIG. 7 is a shaded perspective view of a volume generated by the locator member outside of a hub as it rotates or sweeps around longitudinal axis A.
Figure 8:
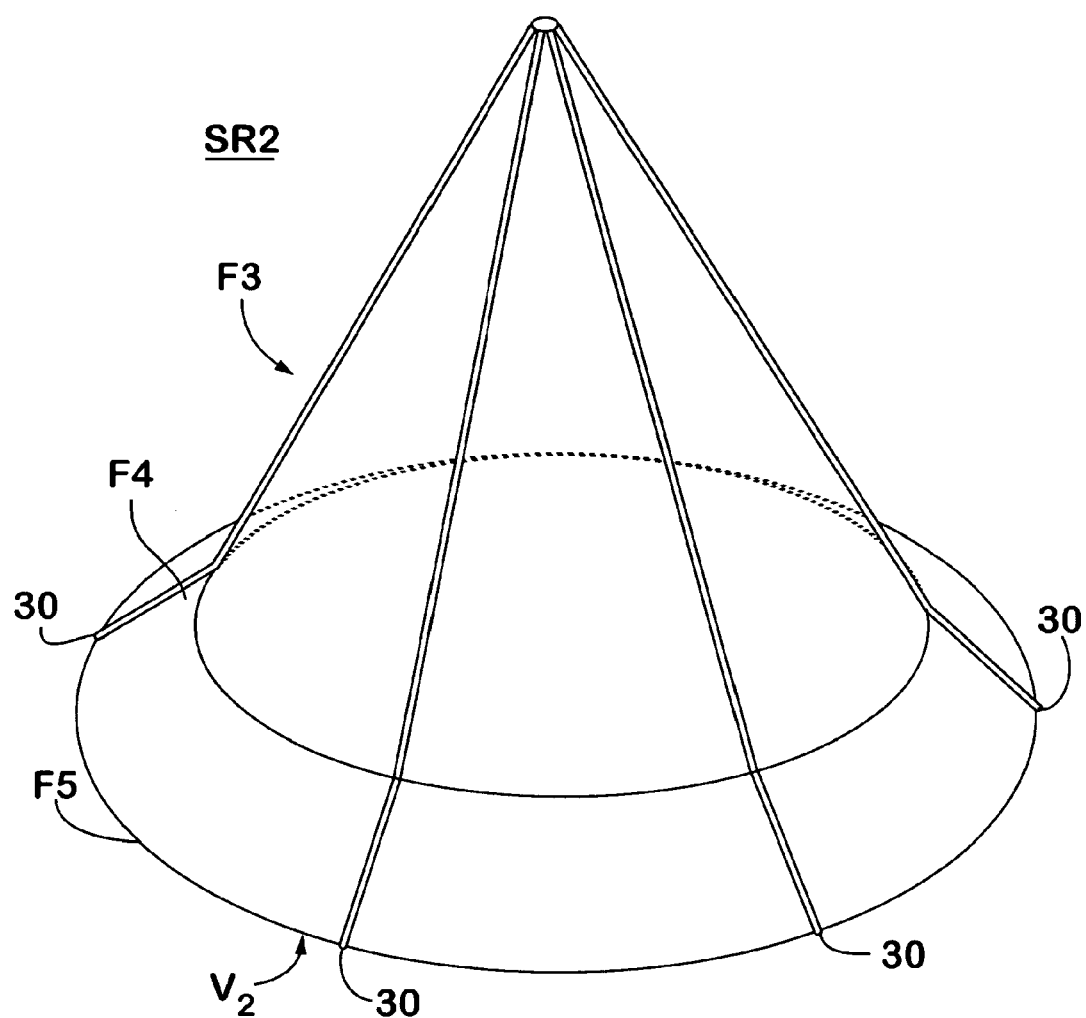
FIG. 8 is a shaded perspective view of a volume generated by the anchor member outside the hub as the anchor member is rotated or sweeps around the longitudinal axis A.

Referring to FIG. 7, the locators 20 are illustrated has being bounded by a first compound surface of revolution SR1 about axis A by rotating one of the locators 20 about axis A for 360 degrees. The first compound surface of revolution SR1 includes a portion of a truncated hyperboloid H, first frustum F1, second frustum F2, and cylindrical surface C1. With reference to FIG. 8, the anchors 30 are illustrated as being bounded by a second compound surface of revolution SR2 about axis A by rotating one of the anchors 30 about axis A for 360 degrees. The second compound surface of revolution SR2 defined by the anchors 30 includes a third, fourth and fifth frustums F3, F4, and F5, respectively.

Figure 9:
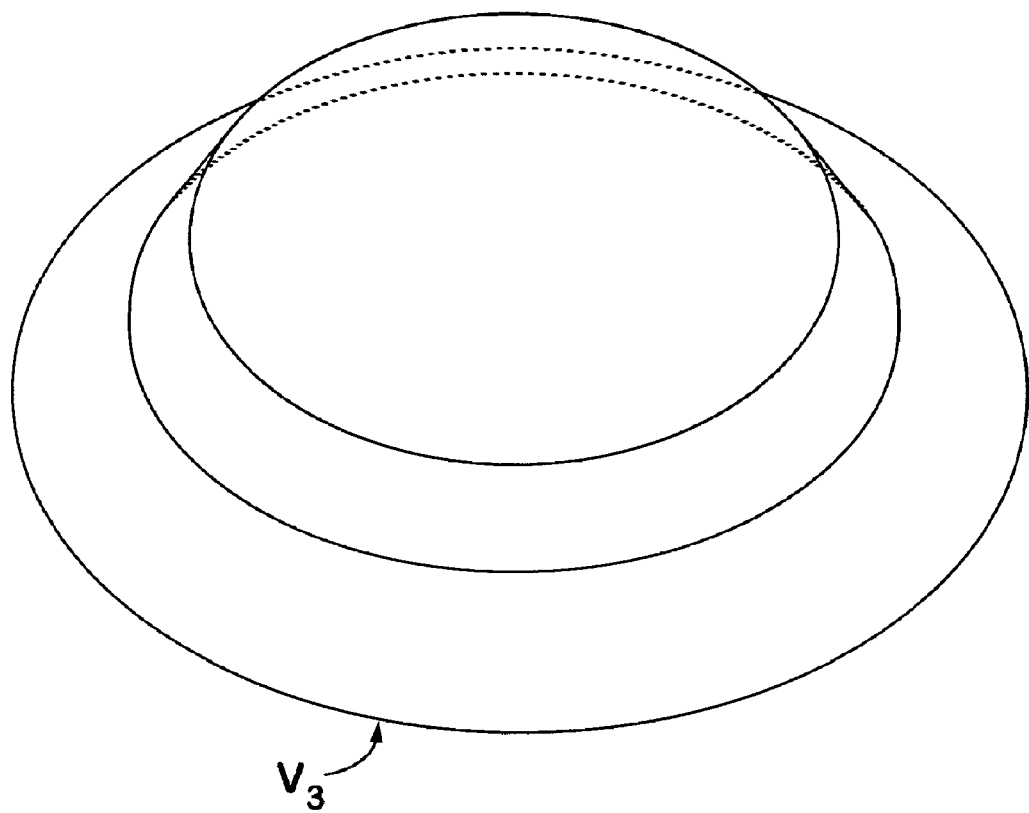
FIG. 9 illustrate the volume of the anchor member visible outside the volume of the locator member.

Several design parameters are believed to allow the preferred embodiments to achieve various advantages over the known filters. The various advantages include, for example, resisting migration of the filter 100 once installed, greater filter volume, and better concentricity with respect to the inner wall of the blood vessel. A number of design parameters may be adjusted to effect performance and fit characteristics of the filter, including, for example, the ratio of the volume $V_1$ defined by the first surface of revolution SR1 to the volume $V_2$ defined by the second surface of revolution SR2, which may be at least 0.92, preferably about 1.0, and most preferably about 0.99. Also, approximately 15% or more of the volume $V_2$ may be surrounded by the volume $V_1$, preferably at least 25% of the volume $V_2$ may be surrounded by the volume $V_1$, and most preferably, about 35% of the volume $V_2$ may be surrounded by volume $V_1$ so that the portion of volume $V_2$ that is not surrounded by volume $V_1$ (i.e., the volume of $V_1$ outside the first volume $V_1$), shown as volume $V_3$ in FIG. 9, is about 0.4 cubic inches. Also, it has been discovered that, in the preferred embodiments, as the cross-sectional area of the hook is increased, the filter 100 tends to resist dislodgement when installed in a simulated blood vessel. Similarly, when the radius of curvature $R_2$ is decreased, while keeping other parameters generally constant, the resistance to dislodgement in a simulated blood vessel is increased.

The material for the filter may be any suitable biocompatible material such as, for example, polymer, memory polymer, memory metal, thermal memory material, metal, metal alloy, or ceramics. Preferably, the material may be Elgiloy, and most preferably Nitinol which is a thermal shape memory alloy.

The use of a shape memory material, such as Nitinol, for the locator and anchor members facilitates collapsing the filter radially inward from its normally expanded (i.e., unconstrained) configuration toward its longitudinal axis into a collapsed configuration for insertion into a body vessel. The properties of Nitinol allow the filter members to withstand enormous deformations (e.g., 8 times as much as stainless steel) without having any effect of the filter ability to recover to the pre-determined shape. This is due to the crystal phase transitions between rigid austenite and softer martensite. This phenomenon enables the implant to be loaded into a very small diameter sheath for delivery, which significantly reduces the trauma and complications to the insertion site.

Transition between the martensitic and austenitic forms of the material can be achieved by increasing or decreasing the material deformation above and below the transition stress level while the material remains above the transition temperature range, specifically $A_f$. This is particularly important in the case of the hooks, as they may be deformed significantly (hence, becoming martensitic) while the filter is challenged by clots. The super-elastic properties will allow the hooks to re-assume their intended shape as soon as the load is released (e.g., the clot breaks down).

The hooks may be retrieved from the Inferior Vena Cava ("IVC") wall during the filter removal when longitudinal force is applied to the hub 10 in the direction of the BF (i.e., towards the hub 10 of the filter). Under this concentrated stress, the hooks will straighten and transition to the martensitic state, thereby becoming super-elastic. Thus the hooks 40 are designed to bend toward a substantially straight configuration when a specific hook migration force is applied and spring back to their original shape once the hook migration force is removed.

Alternatively, a reduction in temperature below the $A_f$ temperature can be applied to the shape memory material to cause a change in the crystalline phase of the material so as to render the material malleable during loading or retrieval of the filter. Various techniques can be used to cause a change in crystalline phase such as, for example, cold saline, low temperature fluid or thermal conductor.

By virtue of the characteristics of thermal shape memory material, the locator and anchor members can be cooled below the martensitic-to-austenitic transition temperature, and then straightened and held in a collapsed, straight form that can pass through a length of fine plastic tubing with an internal diameter of approximately 2 millimeters (mm), e.g., a #8 French catheter. In its high temperature form (as in a mammalian body), the filter 10 recovers to a preformed filtering shape as illustrated by FIG. 1. Alternatively, the locator and/or anchor members may be made of wires of spring metal which can be straightened and compressed within a catheter or tube and will diverge into the filter shape of FIG. 1 when the tube is removed.

The deployed shapes and configurations of the filter members can be set (imprinted with a memory shape) by annealing the members at high temperature (e.g. approximately 500° C.) while holding them in the desired shape. Thereafter, whenever the filter is in the austenitic form (i.e., at a temperature above the martensitic-to-austenitic transition temperature or $A_f$ temperature), the members return to the memory shape. Example methods for setting the high-temperature shape of filters are disclosed in U.S. Pat. No. 4,425,908, the contents of which are hereby incorporated by reference in their entirety.

In the high-temperature form of the shape memory material, the filter has generally coaxial first and second filter baskets or sieves, each filter basket being generally symmetrical about the longitudinal axis of the filter with both filter baskets being concave relative to the filter leading end.

Figure 3:
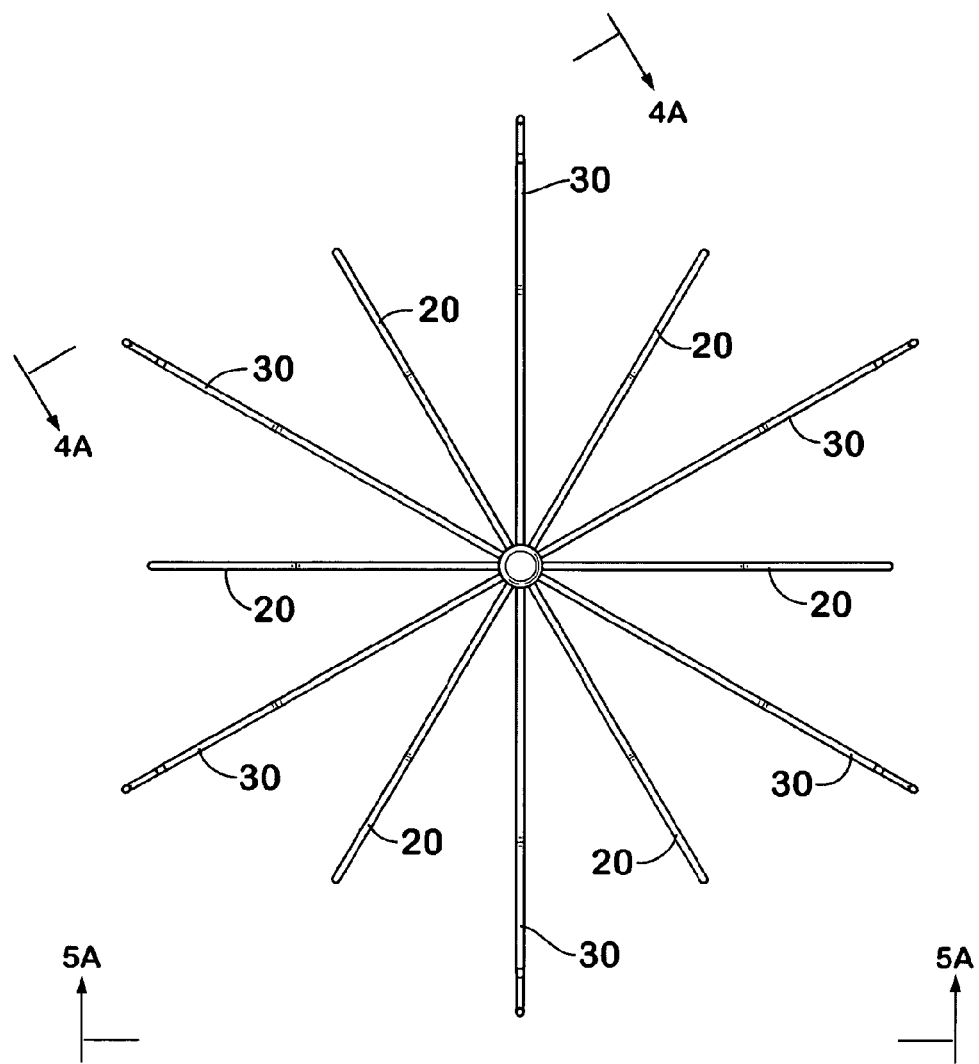
FIG. 3 is a plan view of the filter of FIG. 1 on longitudinal axis A.

The sieve $V_2$ formed by anchor members 30 is the primary filter and can be up to twelve circumferentially spaced anchor members 30. Six anchor members 30 are shown in the embodiment illustrated in the figures. The anchor members may be of equal length, but may be of different length so that the hooks 40 at the ends of the wires will fit within a catheter without becoming interconnected. The anchor members 30, in their expanded configuration illustrated in FIG. 1 (i.e., unconstrained in the high temperature form), are at a slight angle to the vessel wall, preferably within a range of from ten to forty-five degrees, while the hooks 40 penetrate the vessel wall to anchor the filter against movement. The anchor members 30 are radially offset relative to the locator members 20 and may be positioned radially halfway between the locator members 20 and also may be circumferentially spaced by sixty degrees of arc as shown in FIG. 3. The locator members 20 form sieve $V_1$. Thus, the combined filter sieves $V_2$ and $V_1$ can provide a wire positioned radially about the hub 10, such as at every thirty degrees of arc at the maximum divergence of the filter sections. With reference to the direction of blood flow BF shown by the arrow in FIGS. 2 and 4A, in the illustrated embodiment, the filter section $V_2$ forms a frustum toward the hub 10 of the filter 100 while the filter section $V_1$ forms a generally frustum-like concave sieve with its geometric center proximate the terminal end 12 of the hub 10. In the preferred embodiments, the volume $V_1$ of the surface SRI may be between about 0.3 and about 1.1 cubic inches, preferably about 0.7 cubic inches and the volume $V_2$ of the surface SR2 may be between about 0.3 and about 1.1 cubic inches, preferably about 0.7 cubic inches.

The structure of the hooks 40 is believed to be important in resisting migration of the filter once installed while allowing for removal from the blood vessel after installation. As in the case of hooks formed on the anchor members of known permanent vena cava filters, these hooks 40 penetrate the vessel wall when the filter 100 is expanded to anchor the filter in place and prevent filter migration longitudinally within the vessel in either direction. However, when the hooks 40 are implanted and subsequently covered by the endothelium layer, they and the filter can be withdrawn without risk of significant injury or rupture to the vena cava. Minor injury to the vessel wall due to hook withdrawal such as damage to the endothelial layer or local vena cava wall puncture is acceptable.

To permit safe removal of the filter, the juncture section 40S may be considerably reduced in cross section relative to the thickness t2 or cross section of the anchor member 30 and the remainder of the hook 40. The juncture section 40S can be sized such that it is of sufficient stiffness when the anchor members 30 are expanded to permit the hook 40 to penetrate the vena cava wall. However, when the hook is to be withdrawn from the vessel wall, withdrawal force in the direction of blood flow BF will cause flexure in the juncture section 40S so that the hook tip 40T moves toward a position parallel with the axis A (i.e., the hook straightens). With the hooks so straightened, the filter can be withdrawn without tearing the vessel wall while leaving only small punctures. In an embodiment, the anchor member 30 has a cross-sectional area of about 0.00013 squared inches, and the hook 40, particularly the curved junction section 40S has a cross-sectional area of about 0.000086 squared inches.

With reference to FIG. 6, it will be noted that the entire hook 40 can be formed with a cross section $t_3$ throughout its length that is less than that of the locator 20 members (which have thickness $t_1$) or anchor members 30 (which have thickness $t_2$). As a result, an axial withdrawal force will tend to straighten the hook 40 over its entire length. This elasticity in the hook structure is believed to prevent the hook from tearing the vessel wall during withdrawal.

As previously indicated, while it is possible that the filter could be made from ductile metal alloys such as stainless steel, titanium, or Elgiloy, it is preferable to make it from Nitinol. Nitinol is a low modulus material that allows the locator and anchor members of the device 100 to be designed to have low contact forces and pressures while still achieving sufficient anchoring strength to resist migration of the device. The force required to cause opening of the hooks 40 can be modulated to the total force required to resist filter migration. This is accomplished by changing the cross sectional area or geometry of the hooks, or by material selection, as discussed above.

In addition to temperature sensitivity, when in the high temperature austenitic state, Nitinol is also subject to stress sensitivity that can cause the material to undergo a phase transformation from the austenitic to the martensitic state while the temperature of the material remains above the transition temperature. By reducing the cross sectional area of a portion or all of the hooks 40 relative to that of the anchor members 30 or locator members 20, stress will be concentrated in the areas of reduced cross section when longitudinal force is applied to the hub 10 in the direction of the BF (i.e., towards the hub 10 of the filter) such as to remove the filter. Under this concentrated stress, the reduced cross section portions of the hooks may transition to the martensitic state, thereby becoming elastic so that they straighten. Thus the hooks 40, whether formed of Nitinol, Elgiloy, spring metal or plastic, are designed to bend toward a substantially straight configuration when a specific hook migration force is applied and spring back to their original shape once the hook migration force is removed.

The force or stress that is required to deform the hooks 40 can be correlated to the force applied to each hook of the device when it is fully occluded and the blood pressure in the vessel is allowed to reach 50 millimeters of mercury (mm Hg) in a test stand. The test stand (not shown) can be configured to have a length of tubing (with various internal diameters) to allow a filter to be suitably attached thereto. The tubing is connected to another tubing having a terminal end exposed to ambient atmosphere and marked with gradations to indicate the amount of pressure differential across the filter, which is related to the force being applied to each anchor of the filter 100. This force is approximately at least 70 grams on each anchor of a six-anchor device for at least 50 millimeters Hg pressure differential in a 28 mm vessel. The desired total migration resistance force for the filter is believed to be approximately 420 grams for the embodiment of a vena cava filter for an adult human subject, and more anchor members 30 with hooks 40 can be added to lower maximum migration force for each hook. The load on the filter would be correspondingly smaller in vessels of smaller diameter. Preferably the hooks 40 perform as an anchoring mechanism at a predetermined filter migration resistance force within a range of about 10 mm Hg up to about 150-200 mm Hg. Having maintained its geometry at a predetermined filter migration resistance force within this range, the hook 40 preferably begins to deform in response to a higher force applied in the direction of the hub, i.e., the filter trailing end TE with respect to blood flow, and release at a force substantially less than that which would cause damage to the vessel tissue. It is the ability of the hook to straighten somewhat that allows for safe removal of the preferred embodiment filters from the vessel wall.

After the filter 100 has remained in place within a blood vessel for a period of time in excess of two weeks, the endothelium layer will grow over the hooks 40. However, since these hooks 40, when subjected to a withdrawal force in the direction of the hub (i.e., toward the trailing end TE) become substantially straight sections of wire oriented at a small angle to the vessel wall, the filter can be removed leaving only six pin point lesions in the surface of the endothelium. To accomplish this, a catheter such as, for example, the unit described and shown in U.S. Pat. No. 6,156,055, which is incorporated by reference herein, or similar retrieval unit is inserted over the hub 10 and into engagement with the locator members 20. While the hub 10 is held stationary, the catheter may be moved downwardly, forcing the locator members 20 to fold towards the axis A, and subsequently engaging the anchor members 30 and forcing them downwardly thereby withdrawing the hooks 40 from the endothelium layer. Then the hub 10 may be drawn into the catheter to collapse the entire filter 100 within the catheter. When the filter is formed from shape memory material, cooling fluid (e.g., chilled saline) may be passed through the catheter during these steps to aid in collapsing the filter.

The primary objective of the hooks 40 is to ensure that the filter does not migrate during normal respiratory function or in the event of a massive pulmonary embolism. Normal inferior vena cava (IVC) pressures are believed to be between about 2 mm Hg and about 8 mm Hg. An occluded IVC can potentially pressurize to 35 mmHg below the occlusion. To ensure filter stability, a 50 mm Hg pressure drop across the filter may therefore be chosen as the design criteria for the filter migration resistance force for the removable filter 100. When a removal pressure is applied to the filter that is greater than at least 50 millimeters Hg, the hooks 40 will deform and release from the vessel wall. The pressure required to deform the hooks can be converted to force by the following calculations.

Since 51.76 mm Hg=1.0 pounds per square inch (psi), 50 mm Hg=0.9668 psi

For a 28 mm vena cava:

$$A = \frac{\pi}{4}(28)^2 \text{ mm}^2 = 615.4 \text{ mm}^2 = 0.9539 \text{ inches}^2$$

Migration force is calculated by:

$$P = \frac{F}{A} \quad F = P \times A$$

0.9668 psi×0.9539 inches²=0.9223 pounds=418.7 grams

It should be noted that as the vena cava diameter increases so does the force required to resist at least 50 millimeters Hg of pressure. Depending on the number of filter hooks, the strength of each can be calculated. For a device that has six hooks:

$$\text{Hook Strength} = \frac{\text{Filter Migration Resistance Force}}{\text{Number of Hooks}} = \frac{418.7}{6} = 69.7 \text{ grams}$$

In other words, each hook must be capable of resisting approximately at least 70 grams of force for the filter 100 to resist at least 50 millimeters Hg pressure gradient in a 28 mm vessel.

To prevent excessive vessel trauma each individual hook needs to be relatively weak. By balancing the number hooks and the individual hook strength, minimal vessel injury can be achieved while still maintaining the at least 50 millimeters Hg pressure gradient criteria, or some other predetermined pressure gradient criteria within a range of from 10 mmHg to 150 mmHg.

Referring to FIG. 4A, the anchor members 30 may be angled outwardly from the anchor joint or bend AJ1 adjacent to but spaced from the outer end of each anchor member 30. When the anchor members 30 are released from compression in a catheter or other tube into a body vessel, this bend in each anchor member insures that the hooks 40 are, in effect, spring loaded in the tube and that they will not cross as they are deployed from the tube. Since the anchor members 30 angled outwardly from the shoulders 30, the hooks 40 are rapidly deployed outwardly as the insertion tube is withdrawn.

In another embodiment, bio-active agents can be incorporated with the blood filter, such as by way of a coating on parts of the filter, or dissolvable structures on, within or attached to the filter. Bio-active agent may be included as part of the filter in order to treat or prevent other conditions (such as infection or inflammation) associated with the filter, or to treat other conditions unrelated to the filter itself. More specifically, bio-active agents may include, but are not limited to: pharmaceutical agents, such as, for example, anti-proliferative/antimitotic agents including natural products such as vinca alkaloids (i.e. vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) lib/Ilia inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), and trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (e.g., breveldin); anti-inflammatory agents, such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents, such as vascular endothelial growth factor (VEGF), fibroblast growth factor (FGF); angiotensin receptor blockers; nitric oxide donors; anti-sense oligionucleotides and combinations thereof; cell cycle inhibitors, such as mTOR inhibitors, and growth factor receptor signal transduction kinase inhibitors; retenoids;

cyclin/CDK inhibitors; HMG co-enzyme reductase inhibitors (statins); and protease inhibitors.

A filter delivery unit (not shown) such as, for example, the unit described in U.S. Pat. No. 6,258,026, which is incorporated by reference herein, is adapted to deliver the filter 100 through a catheter or delivery tube to a generally centered position within a body vessel, as described in further detail in the above mentioned patent. Preferably, the delivery system may be the delivery system shown and described in US 2009/0318951 A1, which is hereby incorporated by reference in their entirety into this application.

In an embodiment, a radio-opaque material can be incorporated in a portion of the filter, preferably the hub 10 of the filter. As used herein, a radio-opaque material is any material that is identifiable to machine or human readable radiographic equipment while the material is inside a mammal body, such as, by way of example but not by way of limitation, gold, tungsten, platinum, barium sulfate, or tantalum. The use of a radio-opaque material in the filter permits the clinician to locate the filter within a blood vessel of the subject using radiographic equipment. Radio-opaque material may be in the form of an additional structure added to the hub, such as a cap, sleeve, shim, wire or braze included around or in the hub assembly. Alternatively, the hub itself may be formed of a radio-opaque alloy.

Figure 10:
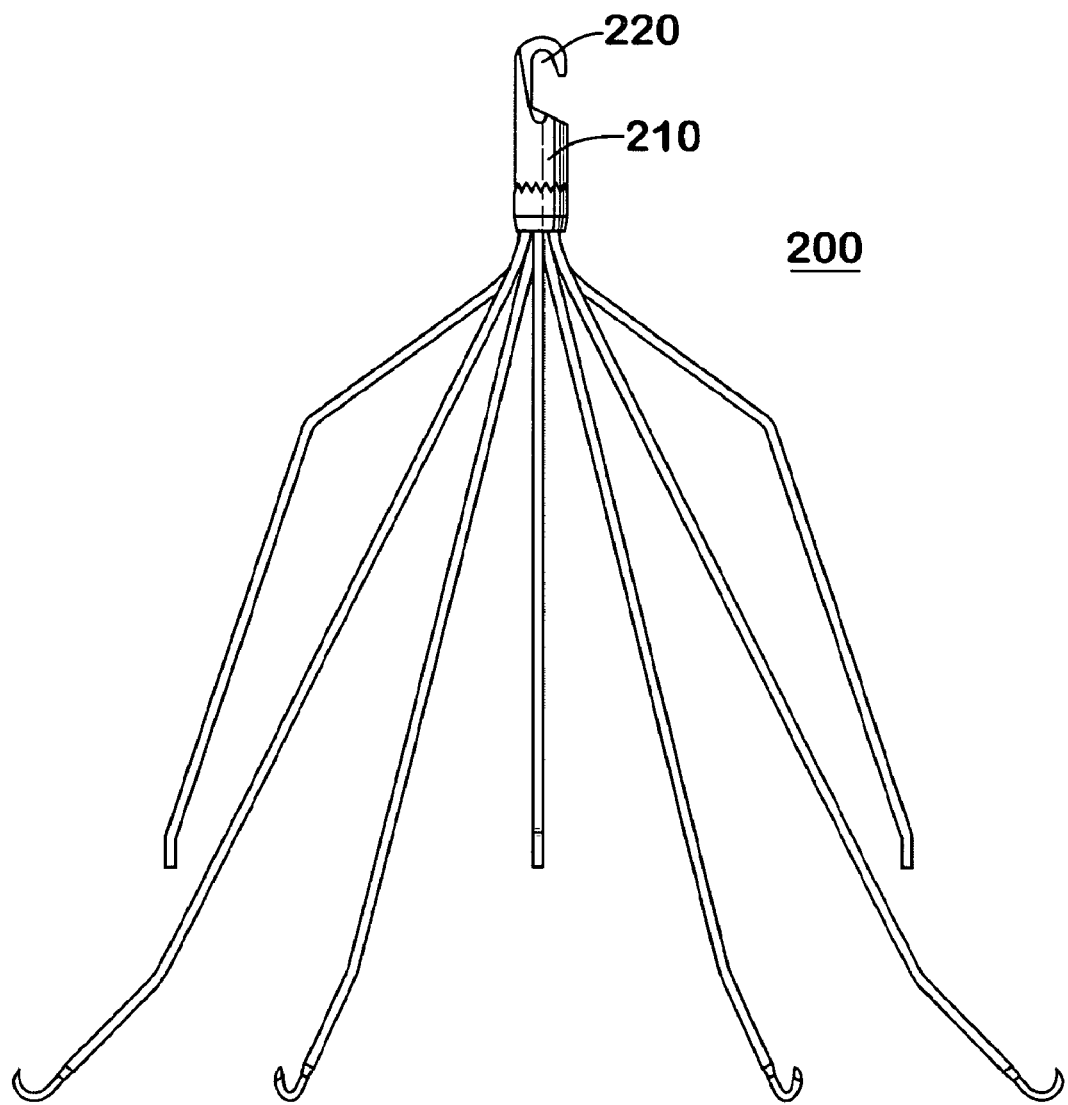
FIGS. 10-14 illustrate yet another preferred embodiment having a retrieving hook portion.
Figure 11:
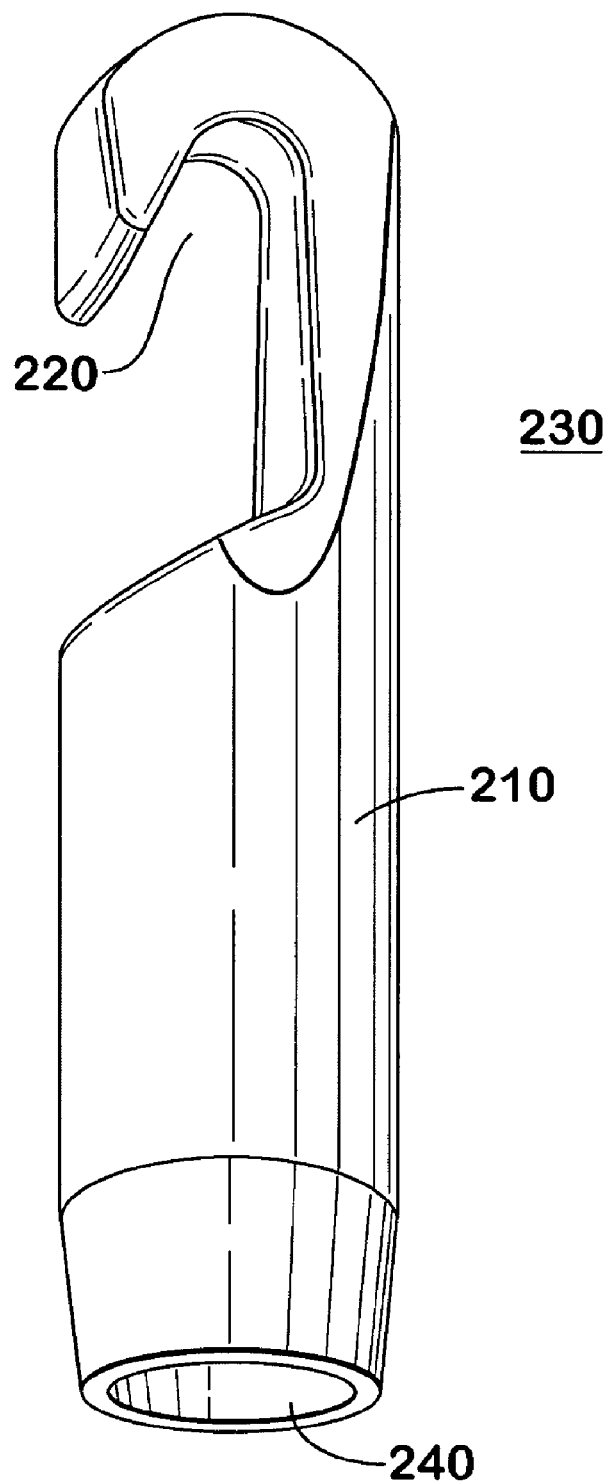
Figure 12:
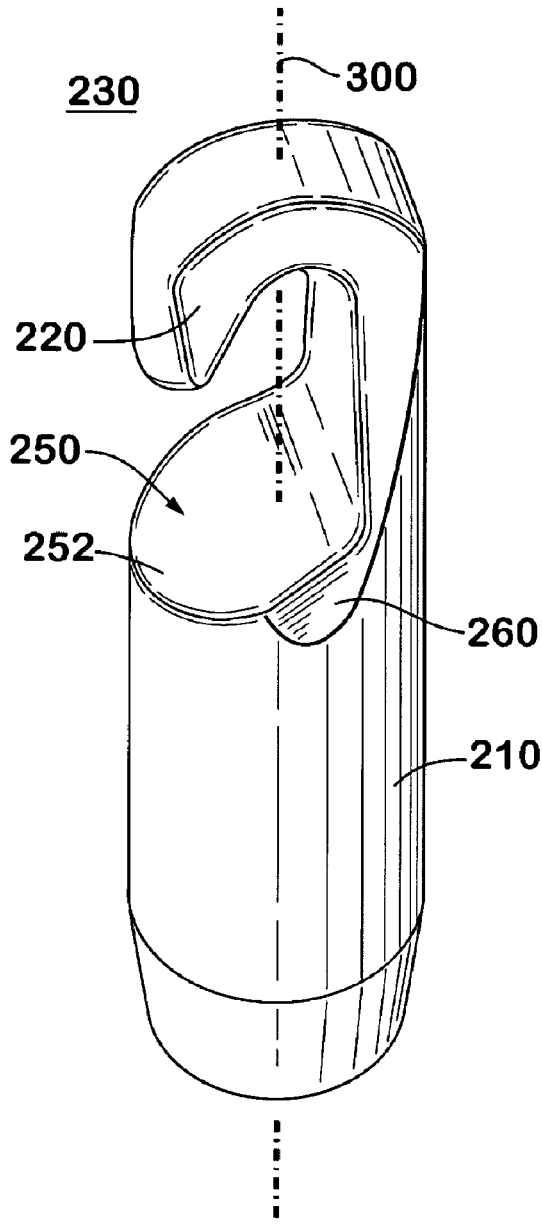
Figure 13:
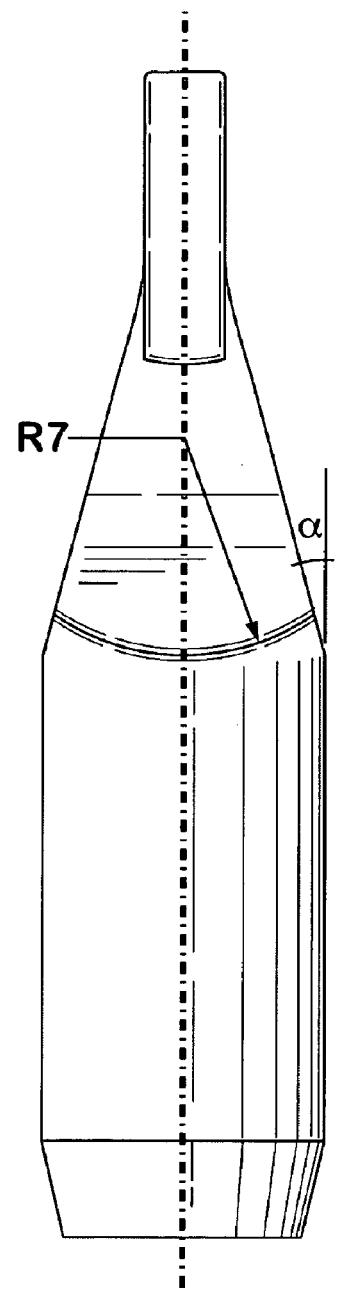
Figure 14:
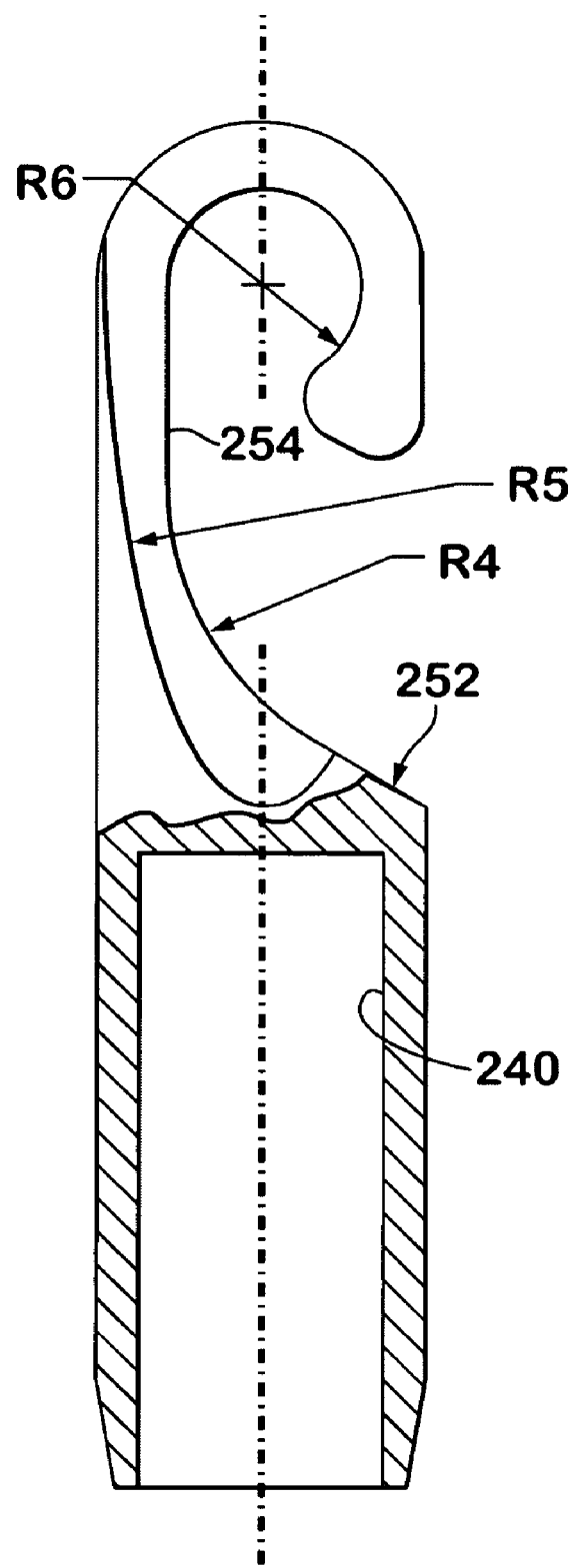

Instead of a hub 10, as in the above described embodiments, a retrieving hook can be provided as part of filter device 200, as in the embodiment shown in FIG. 10. The filter device 200 includes a hub 210 with a retrieving hook 220. The hook 220 is configured for use by a snaring device to retrieve the filter 200 from a subject. Referring to FIGS. 11 and 12, the retrieving hook 220 can be formed as a monolithic member 230 with the hub 210 or as a separate member joined to the hub 210 by a suitable technique, such as, for example, EDM, laser welding, plasma welding, welding brazing, welding, soldering, or bonding. In a preferred embodiment, the member 230 can be a machined billet member with a blind bore 240 formed through a portion of the hub 210. The hook portion 220 includes ramped surfaces 250 and 260 that are believed to be advantageous in allowing the filter 200 to be retrieved without binding at the catheter opening due to an offset entry position of the filter 200. In other words, there may be circumstances during removal procedures where the axis 300 of the member 230 is not generally parallel or aligned with a longitudinal axis of the catheter retrieving device. In such cases, the greater the retention force, it is believed that the greater the likelihood of the hook being snagged on the catheter inlet opening thereby complicating the filter retrieval process. By virtue of the ramps 250 and 260, it is believed that binding or snagging is substantially reduced. In particular, as shown in FIGS. 13 and 14, the ramp 250 includes a radius of curvature R4 coupled to flat portions 252 and 254. The flat portion 254 can be coupled to a hook portion 256 which has a radiused surface R6. As shown in FIG. 13, the flat portion 252 is coupled to another radiused portion R7. It should be noted that the drawings provided herein are to scale relative to every part illustrated in each drawing.

A range of values may be used for the aforementioned dimensional parameters in order to provide a retrieval hook 230 that is capable of retaining portions of the locator and anchor members 20 and 30 within blind hole 240. For example, a smaller filter may have smaller dimensions so that the retrieval hook 230 does not present undue blockage in the vein, than a filter intended to be placed in a large vein or vessels, such as an adult vena cava or other vessel. Further, the retrieval hook 230 may be made from or include a radio-opaque material to allow a clinician to locate the hook within a subject using radiographic equipment, such as to aid in engaging the hook with a retrieval mechanism.

Figure 15:
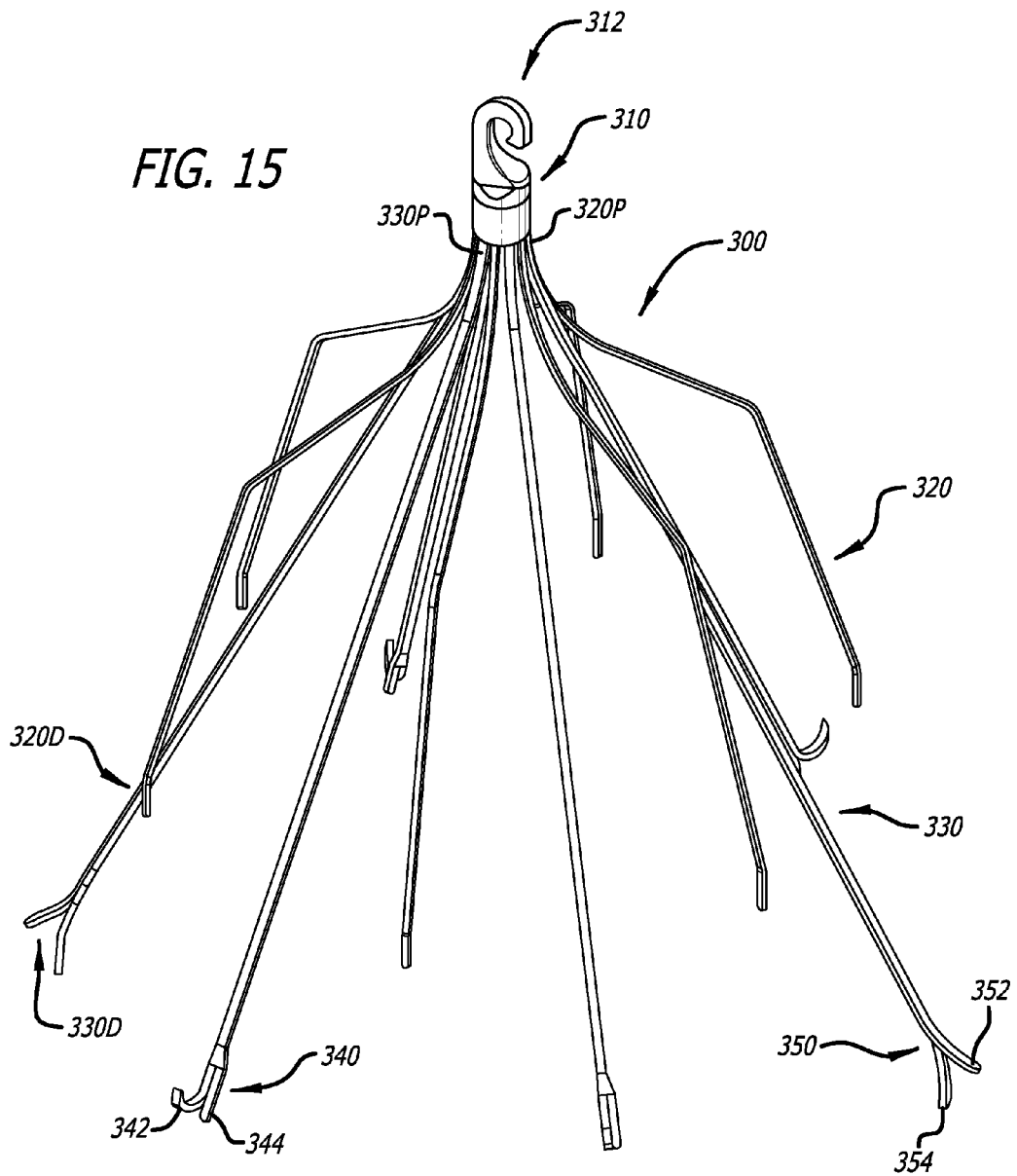
FIG. 15 is a perspective view of an embodiment of a blood filter.

In an embodiment illustrated in FIG. 15, a filter 300 is laser cut from a metal tube and includes a hub 310, locator member 320, and anchor member 330. The locator member 320 includes a proximal locator end 320P and a distal locator end 320D, similar to locator member 20 of FIG. 1. Likewise, the anchor member 330 includes a proximal anchor end 330P and a distal anchor end 330D. The distal anchor end 330D of each anchor member 330 includes an extension member. In the illustrated embodiment, four of the six anchor members include a cranial extension 340 and two of the six anchor members include a caudal extension 350. In other embodiments, the extension members can be distributed differently. For example, the number of anchor members with cranial extension 340 can be less than or more than four, and the number of anchor members with caudal extension 350 can be one, three, or more. Both the cranial extension 340 and caudal extension 350 bifurcate into a penetration member and a penetration limiter. The penetration member is designed to penetrate the vessel wall while the penetration limiter is designed to limit the penetration of the penetration member.

Figure 16A:
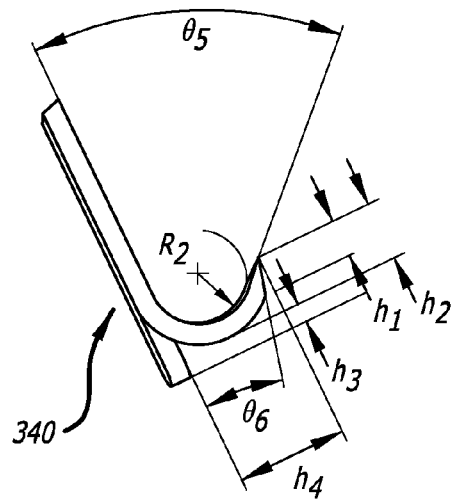
FIG. 16A is a close-up view of a blood filter cranial extension in FIG. 15.

FIG. 16A shows a close-up view of the cranial extension 340 from FIG. 15. In an example embodiment suitable for an adult human vena cava filter, when the filter is at the temperature of the subject and unconstrained, the radius of curvature $R_2$ is about 0.03 inches; the length $h_1$ is about 0.02 inches; the length $h_2$ is about 0.04 inches; the length $h_3$ is about 0.01 inches; the length $h_4$ is about 0.07 inches; the angle $\theta_5$ is about 46 degrees; the angle $\theta_6$ is about 15 degrees. It should be noted that the values given herein are approximate, representing a dimension within a range of suitable dimensions for the particular embodiment illustrated in the figures, and that any suitable values can be used as long as the values allow the filter to function as intended in a blood vessel of a subject. The geometry and bending of the cranial hook 342 will facilitate removal from the vessel, although it should be noted that the bending may be of various degrees less than substantially straight. Referring to the pressure required to deform the cranial hook 342 using the calculations above, because the number of cranial hooks 342 in filter 300 numbers four, the required hook strength is about 104.7 grams (418.7/4), meaning that each hook must be minimally capable of resisting approximately 105 grams of force for the filter 300 to resist at least 50 millimeters Hg pressure gradient in a 28 mm vessel.

Figure 16B:
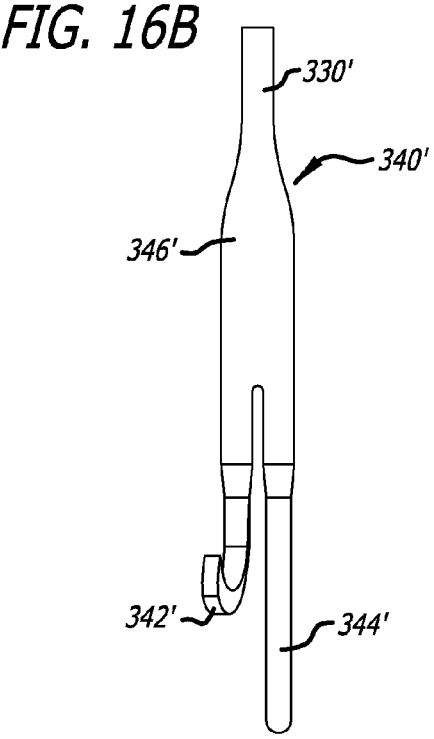
FIGS. 16B-C are depictions of exemplary cranial extensions.
Figure 16C:
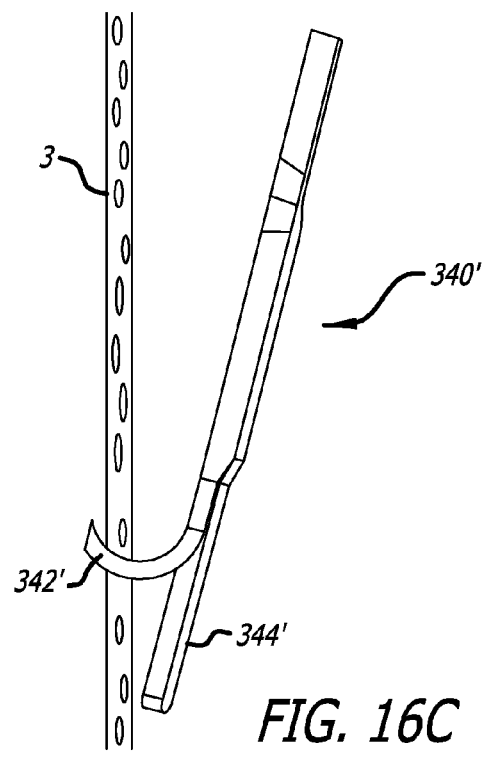

A depiction of an exemplary cranial extension is illustrated in FIGS. 16B-16C. The cranial extension 340' bifurcates from a base 346' into a cranial hook 342' and a cranial limiter 344'. The base 346' has a width that is greater than the anchor member 330' from which it extends in the embodiment shown to provide a greater width to both the cranial hook 342' and cranial limiter 344', and also to assist the cranial limiter 344' in limiting penetration of the cranial hook 342'. In the embodiment shown in FIG. 16B, both the cranial hook 342' and cranial limiter 344' have a tapered portion extending from the base bifurcation, but such tapered portion is optional. The cranial hook 342' prevents cranial movement of the filter toward the heart following deployment and is configured in one embodiment with the design and characteristics of hook 40 as illustrated in FIG. 6 and described herein. The cranial hook 342' may have a reduced thickness relative to the anchor member 330', which is formed through local modification prior to or after filter forming to achieve desired stiffness. For example, when formed from a tube, the flexibility of the cranial hook 342' can be fine-tuned by locally removing material from the inner or outer surface of the tube at the position of the hook 342'. As discussed above in connection with hook 40, the cranial hook 342' can be configured to bend toward a substantially straight configuration when a specific hook migration force is applied, and spring back to an original shape once the hook migration force is removed.

FIG. 16C shows the cranial extension 340' deployed in a body vessel with the cranial hook 342' penetrating a vessel wall 3 and the cranial limiter 344' contacting the vessel wall 3 to prevent excessive penetration of the cranial hook 342'. The configuration of the cranial extension 340' (e.g., through the base width, limiter length, hook flexibility, etc.) limits the penetration distance of the cranial hook 342' while preventing cranial movement. The cranial limiter 344' is formed with a non-penetrating distal end to prevent penetration of the vessel wall 3. However, in some embodiments, the cranial limiter 344' may act as, and/or be configured for, prevention of caudal movement. In the illustrated embodiment, the cranial limiter 344' is essentially straight with respect to the anchor member 330'; however, in other embodiments, the cranial limiter can be curved or angled. The cranial limiter may also include a widened distal end in the form of a tab as shown and discussed in connection with the caudal limiter below.

Figure 17A:
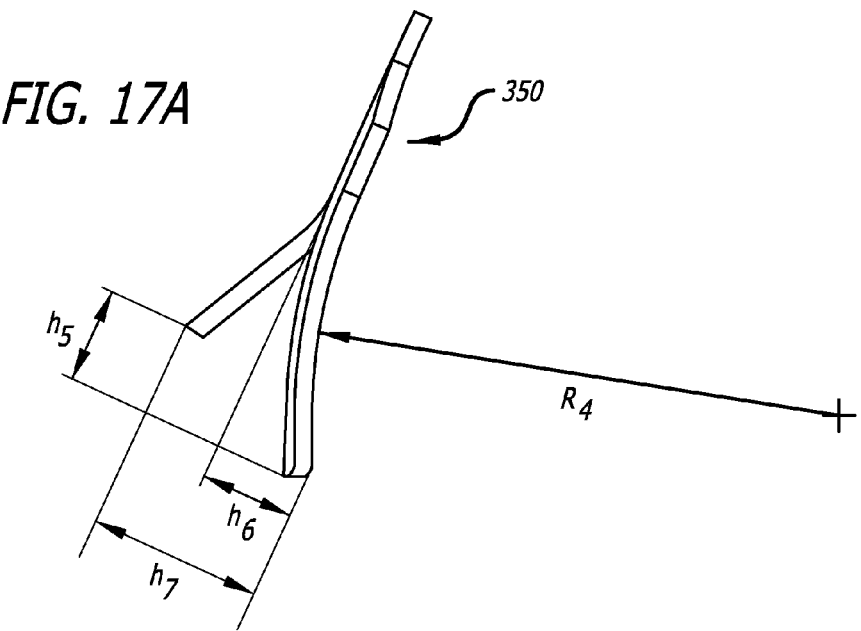
FIG. 17A is a close-up view of a blood filter caudal extension in FIG. 15.

FIG. 17A shows a close-up view of the caudal extension 350 from FIG. 15. In an example embodiment suitable for an adult human vena cava filter, when the filter is at the temperature of the subject and unconstrained, the radius of curvature R4 is about 0.3 inches; the length h5 is about 0.05 inches; the length h6 is about 0.05 inches; the length h7 is about 0.1 inches. It should be noted that the values given herein are approximate, representing a dimension within a range of suitable dimensions for the particular embodiment illustrated in the figures, and that any suitable values can be used as long as the values allow the filter to function as intended in a blood vessel of a subject.

Figure 17B:
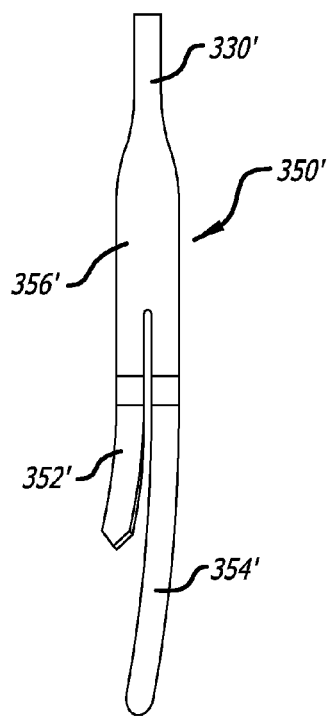
FIGS. 17B-C are depictions of exemplary caudal extensions.
Figure 17C:
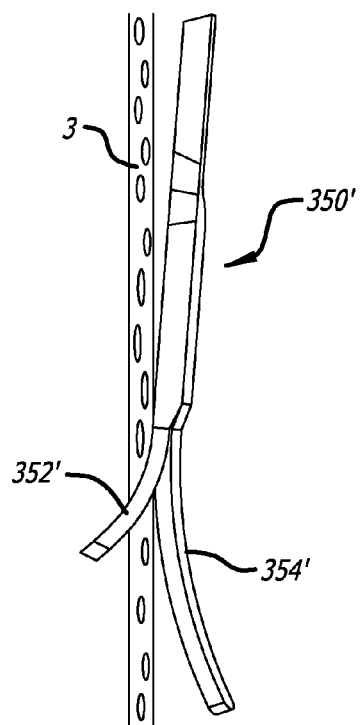

A depiction of an exemplary caudal extension is illustrated in FIGS. 17B-17C. The caudal extension 350' bifurcates from a base 356' into a caudal anchor 352' and a caudal limiter 354'. The base 356' has a width that is greater than the anchor member 330' from which it extends in the embodiment shown to provide a greater width to both the caudal anchor 352' and caudal limiter 354', and also to assist the caudal limiter 354' in limiting penetration of the caudal anchor 352'. In the embodiment shown in FIG. 17B, both the caudal anchor 352' and caudal limiter 354' extend from the base bifurcation with a constant width. However, in other embodiments, both may include a tapered portion similar to that of the cranial extension 340'. The caudal anchor 352' prevents caudal movement of the filter away from the heart following deployment and is configured with a distal blade configured to penetrate the vessel. The caudal anchor 352' may have a reduced thickness relative to the anchor member 330', which is formed through local modification prior to or after filter forming to achieve desired stiffness. For example, when formed from a tube, the flexibility of the caudal anchor 352' can be fine-tuned by locally removing material from the inner surface of the tube at the position of the anchor 352'.

FIG. 17C shows the caudal extension 350' deployed in a body vessel with the caudal anchor 352' penetrating a vessel wall 3 and the caudal limiter 354' contacting the vessel wall 3 to prevent excessive penetration of the caudal anchor 352'. The configuration of the caudal extension 350' (e.g., through the base width, limiter length, etc.) limits the penetration distance of the caudal anchor 352' while preventing caudal movement. The caudal limiter 354' is formed with a non-penetrating distal end to prevent penetration of the vessel wall 3. In the illustrated embodiment, the caudal limiter 354' is curved with respect to the anchor member 330'; however, in other embodiments, the caudal limiter can be straight or angled. The caudal limiter may have a length greater than the caudal anchor, as shown in FIG. 17B. Alternatively, the caudal limiter may be the same length or shorter than the caudal anchor. The caudal limiter may also include a widened distal end in the form of a tab 358 as best seen in FIG. 18.

In one embodiment, in addition to, or instead of, cranial extensions and caudal extensions, the anchor members include an extension having a base that bifurcates into a cranial hook and caudal anchor.

Referring again to FIG. 15, the filter 300 includes six locator members 320 and six anchor members 330 extending from the hub 310 and disposed along a longitudinal axis of the filter 300. The locator members 320 are alternatingly interposed between the anchor members 330 such that each locator member 320 extends from the hub between adjacent pairs of anchor members, and vice versa. However, in other embodiments, the locator members 320 and/or anchor members 330 may be directly adjacent to one another without an intervening anchor member 330 and/or locator member 320. Each of the locator members 320 have essentially the same size and configuration, and include four segments LS1, LS2, LS3, and LS4, as described in more detail below in connection with FIG. 19. While the locator members in the illustrated embodiment do not include hooks or anchors, in other embodiments one or more locator members may include an extension, a hook and/or an anchor as described herein. The total anchor members and locator members in other embodiments can be more or less than the 12 shown in the illustrated embodiment.

Figure 19:
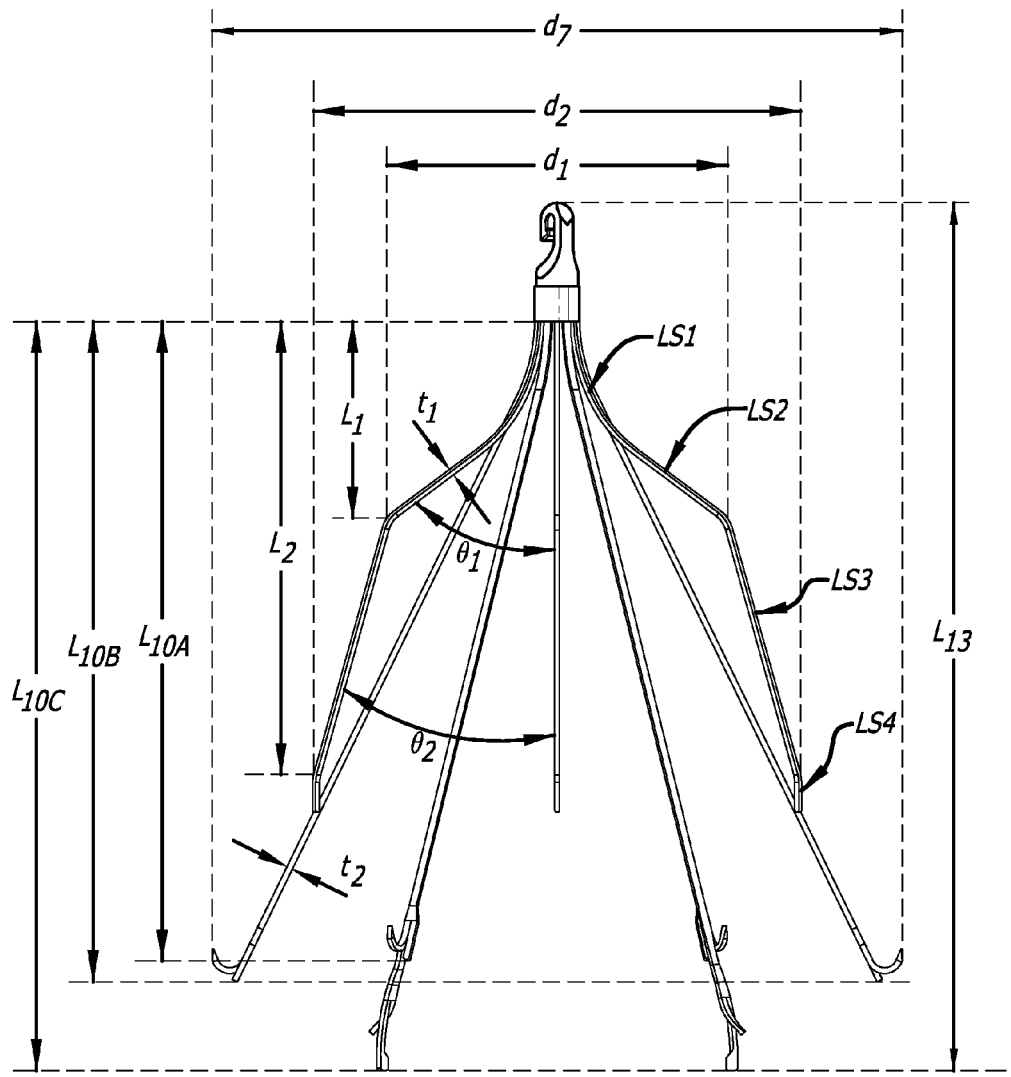
FIG. 19 is another perspective view of the blood filter in FIG. 15, illustrating parameters thereof.

In FIG. 15, the six anchor members 330 have three different lengths measured from the hub 310 along the longitudinal axis of the filter, a first length/distance from the hub 310 is the shortest (i.e., L10A in FIG. 19), a second length/distance from the hub 310 is greater than the first length/distance (i.e., L10B in FIG. 19), and the third length/distance from the hub 310 is greater than both the first and second lengths/distances (i.e., L10c in FIG. 19). In other embodiments, the anchor members may have two different lengths or four or more different lengths. In embodiments in which the anchor members include cranial extensions, caudal extensions, cranial hooks, caudal anchors, or other forms of hooks or anchors, providing different anchor member lengths in a staggered pattern facilitates collapse into a filter constrained or delivery configuration, and also potentially reduces the necessary components of a delivery system (e.g., because the hooks and anchors are staggered and positioned in a compact manner as discussed below with respect to the method of folding, it is possible to deliver the filter without the use of a means of holding or covering the hooks in the delivery sheath). The anchor members 330 have an essentially straight configuration distal of the proximal anchor end 330P, which curves outward from the filter longitudinal axis in the filter expanded configuration. In other configurations, the anchor members 330 may have one or more segments extending along different axes, similar to anchor members 30 discussed above in connection with FIGS. 5A and 5B.

Of the six anchor members 330, two anchor members extend the first distance from the hub 310, two anchor members extend the second distance from the hub 310, and two anchor members extend the third distance from the hub 310. The pair of first length anchor members and the pair of second length anchor members each include cranial extensions at a distal end thereof. The difference between the first length and second length in one embodiment is measured from the tips of the cranial hooks 342 in a filter expanded (unconstrained) configuration, i.e., L14 as shown in FIG. 18. In the embodiment shown in FIG. 18, L14 is approximately 0.05 inches. The pair of third length anchor members each include caudal extensions at a distal end thereof. The combination of anchor members with cranial extensions and caudal extensions prevent both caudal and cranial movement of the blood filter, thereby stabilizing the filter in the deployed position inside of a body vessel.

In the illustrated embodiment of FIG. 15, the pairs of first, second and third length anchor members are positioned opposite from one another about the hub (i.e., 180 degrees). From a top view of the filter in an expanded configuration (e.g., see FIG. 3), using a clock analogy, the pair of anchor members are positioned as follows: when the first length anchor members are positioned at 12 and 6, the pair of second length anchor members are positioned at 4 and 10, and the pair of third length anchor members are positioned at 2 and 8. As described in detail below, this particular respective positioning of the anchor members facilitates the preparation of the filter for loading and delivery. Other possibilities with respect to anchor member positioning with respect to the hub may alternatively be desired, and therefore it should be appreciated that the illustrated embodiment is not intended to be limiting.

As shown in FIG. 19, the locator member 320 is similar in many respects to the locator member 20, including the plurality of locator segments LS1-LS4. However, the locator member 320 has the following dimensional parameters which may differ slightly from the locator member 20 described above. In an example embodiment suitable for an adult human vena cava filter, when the filter is at the temperature of the subject and unconstrained, the radius of curvature $R_8$ is about 0.35 inches; the length L1 is about 0.45 inches; length L2 is about 1.0 inches; distance $d_1$ is about 0.9 inches; distance $d_2$ is about 1.27 inches, the first angle $\theta_1$ is about 57 degrees, the second angle $\theta_2$ is about 17 degrees; and the thickness $t_1$ of the locator member 320 along section LS2 is about 0.0125 inches, and along LS3 is also about 0.0125 inches. The longitudinal distance $L_{10A}$ is about 1.45 inches, $L_{10B}$ is about 1.50 inches, $L_{10C}$ is about 1.70 inches, and $L_{13}$ is about 2.0 inches; $d_7$ is about 1.6 inches; the radius of curvature $R_2$ is about 0.03 inches; and the thickness $t_2$ of the anchor member is about 0.0125 inches. It should be noted that the values given herein are approximate, representing a dimension within a range of suitable dimensions for the particular embodiment illustrated in the figures, and that any suitable values can be used as long as the values allow the filter to function as intended in a blood vessel of a subject.

It should also be noted that although the thickness of the locator member 320 and anchor member 330 is described in an exemplary embodiment as being uniform throughout their lengths (e.g., having the same thickness as the rest of the filter 300), other embodiments include varying thicknesses along the length of the locator member. For example, the locator member and/or anchor member may include segments with different thicknesses or have varying thicknesses along select segments. It is also noted that the widths of the locator member and/or anchor members could similarly vary along their lengths. For example, in one embodiment the width of locator segment LS1 is greater than the other locator segments which have a uniform width. Further, while the anchor members 330 of filter 300 are wider than the locator members 320, in other embodiments, the anchor members and locator members may be the same width, or the locator members may be wider than the anchor members.

As described herein, the filter 300 is cut from a metal tube (e.g., Nitinol). The formation of filter 300 from a tube provides the opportunity to locally reduce thicknesses of sections of the filter, such as the cranial hook 342 and/or the caudal anchor 352. Following the laser cutting of the tube and forming of the filter, electropolishing, chemical etching or other similar processes can be utilized to enhance the surface finish for improved corrosion resistance and a fatigue life. It is also noted that filter 300 could be formed from wires or sheet.

Figure 21A:
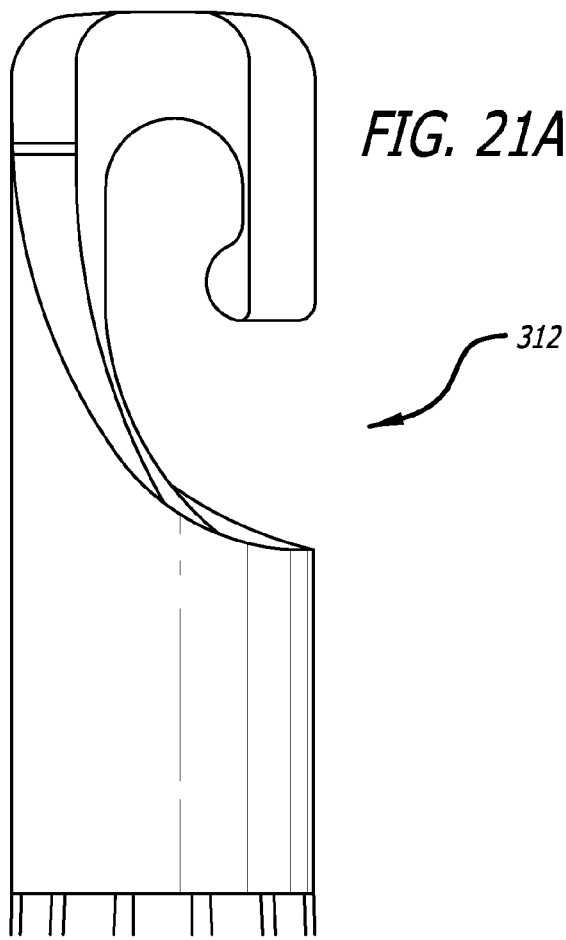
FIGS. 21A-B are close-up views of an alternate embodiment of a retrieval member for the blood filter in FIG. 15.
Figure 21B:
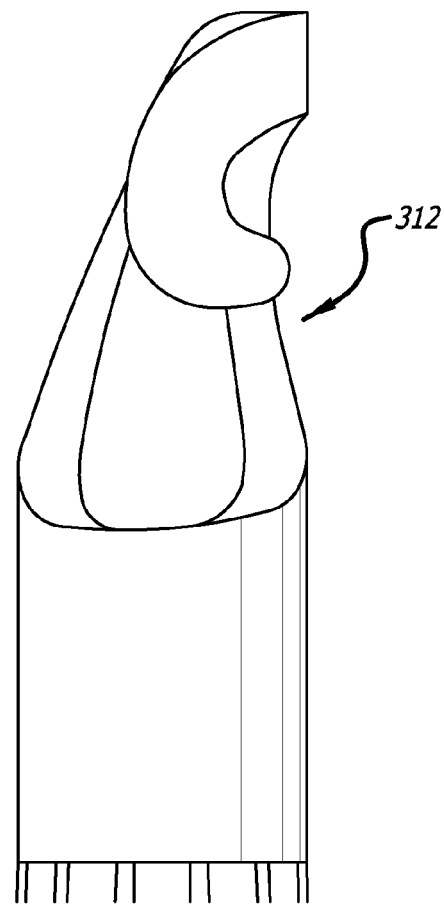

The filter hub 310 can include a retrieval member 312 as shown in FIG. 15. The retrieval member 312 can be formed from a solid rod with an extension 313 that can be inserted into the open end of the hub 310, as shown in FIG. 20, and then welded, crimped or otherwise permanently attached to the hub 310. Alternatively, the retrieval member 312 can be formed directly from the tube from which the filter is formed as shown in FIGS. 21A and 21B. FIG. 21A is a side view of the retrieval member 312 and FIG. 21B is a front view of the retrieval member 312. As can be seen in FIG. 21, any number of patterns and formations can be cut from the tube to enhance the retrievability of the filter 300.

Figure 22:
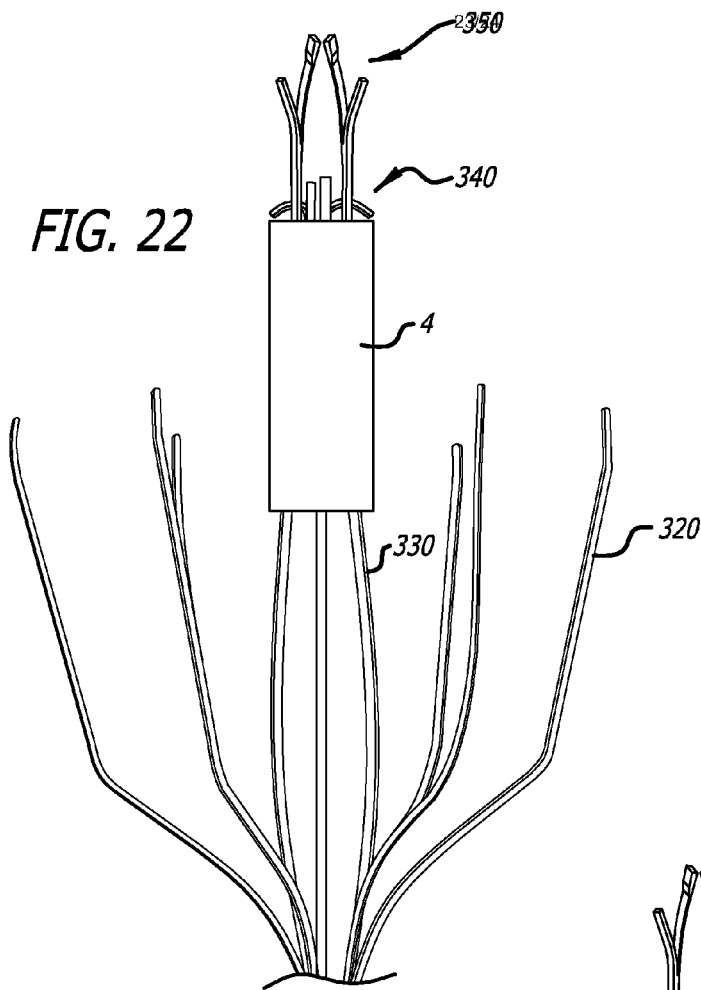
FIG. 22 is a close-up view of a portion of the blood filter of FIG. 15 as it is being prepared for loading and delivery.
Figure 23:
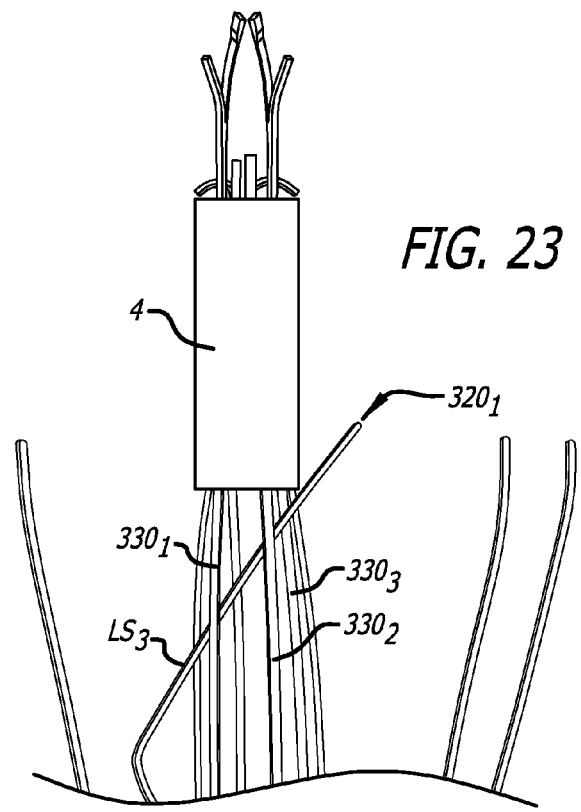
FIG. 23 is a close-up view of a portion of the blood filter of FIG. 15 at another stage of preparation for loading and delivery.

An exemplary method of preparing the filter 300 for loading and delivery is shown in FIGS. 22 to 26. The positioning of the anchor members 330 in relation to each other and the other filter features facilitates collapsing the filter 300 into a low profile, in part due to the staggered lengths of the anchor members 330. The filter 300 includes six anchor members and six locator members, which for reference are numbered successively counterclockwise about the circumference of the hub 310 when viewed from the anchor member distal ends as first, second, third, fourth, fifth, and sixth anchor members, and first, second, third, fourth, fifth, and sixth locator members, where the first locator member is positioned closest clockwise of the first anchor member (i.e., extending between the first anchor member and sixth anchor member). It should be appreciated that the method shown and described is only one example and many variations are possible. For example, while the third segment LS3 of the locator member is described as being positioned behind the anchor member, any length of a locator member or its equivalent component in a blood filter could be so positioned. Further, the positioning order could be varied, as could the positioning of the locator members relative to one another. Further still, rather than positioning a length of locator members behind two anchor members, the length of locator members could be positioned behind one, three, or more anchor members. FIG. 22 shows the filter 300 with the anchor members constrained in a collapsed configuration by a tube 4; however other constraining methods and/or devices are also possible. The tube 4 is slid over the hub 310 toward the anchor member distal ends 330D until the distal end of the tube abuts the cranial hooks on the first length anchor members. The locator members 320 are removed from the tube (if the tube initially covers the ends thereof) so that they are in an expanded configuration as shown in FIG. 22. As shown in FIG. 23, the third locator segment LS3 of the first locator member 3201 is positioned behind (i.e., toward the filter longitudinal axis) the first anchor member 3301 and the second anchor member 3302 such that a distal end of the first locator member 3201 extends between the second anchor member 3302 and the third anchor member 3303. As shown in FIG. 24, the third locator segment LS3 of the second locator member 3202 is then positioned behind the second anchor member 3302 and the third anchor member 3303 such that a distal end of the second locator member 3202 extends between the third anchor member 3303 and the fourth anchor member 3304.

The third locator segment LS3 of the third locator member 3203 is then positioned behind the third anchor member 3303 and the fourth anchor member 3304 such that a distal end of the third locator member 3203 extends between the fourth anchor member 3304 and the fifth anchor member 3305. The third locator segment LS3 of the fourth locator member 3204 is then positioned behind the fourth anchor member 3304 and the fifth anchor member 3305 such that a distal end of the fourth locator member 3204 extends between the fifth anchor member 330s and the sixth anchor member 3306. The third locator segment LS3 of the fifth locator member 320s is then positioned behind the fifth anchor member 3305 and the sixth anchor member 3306 such that a distal end of the fifth locator member 3205 extends between the sixth anchor member 3306 and the first anchor member 3301. Lastly, the third locator segment LS3 of the sixth locator member 3206 is positioned behind the sixth anchor member 3306 and the first anchor member 3301 such that a distal end of the sixth locator member 3206 extends between the first anchor member 3301 and the second anchor member 3302.

In this particular embodiment, in addition to being positioned behind two anchor members, the locator members are positioned such that, when viewed from the distal end of the anchor members 330D, each locator member is under (i.e., crosses under) its previous in number locator member (e.g., the second locator member is positioned under the first locator member). Such a positioning configuration is shown in FIG. 25, which is simplified to show schematically the relative locator member positioning (e.g., only a representative length of the locator member positioned behind the anchor members is shown). In other embodiments, some of the locator members may instead be positioned over adjacent locator members.

Once the locator members 320 are threaded into position, the filter is partially pulled into a delivery sheath or staging sheath 5 as shown in FIG. 26. The positioning of the anchor member extensions is verified to ensure that the anchor members with caudal extensions are surrounded by the anchor members with cranial extensions. In one embodiment, the caudal extensions are positioned such that the caudal limiters are adjacent to each other so that the flat surfaces are together to avoid catching of the caudal anchors upon deployment of the filter. The anchor member positioning is then reviewed to ensure that the cranial hooks are all facing in one direction (e.g., clockwise). In order to position the cranial hooks, for example if the cranial hooks are facing away from the longitudinal axis or in different directions, the filter is twisted as it is pulled into the delivery sheath. The cranial hooks will follow the path of least resistance and will continue twisting until they are circumferentially oriented. In one embodiment, the cranial extensions are oriented such that the cranial hooks lie against the sheath inner wall and the cranial limiters lie away from the sheath inner wall for beneficial distribution of the available volume. Once properly oriented, the filter is completely pulled into the delivery sheath.

In one embodiment, the method of preparing the filter for delivery is generally described in relation to the total number N of anchor members and same number N of locator members extending from the filter hub, the locator members interposed between the anchor members. As with the example above, both the anchor members and locator members are arranged and numbered successively counterclockwise about a circumference of the hub when viewed from a filter distal end such that a given locator member n is positioned immediately clockwise adjacent of a given anchor member n. Also, as with the above example, the anchor members include either a cranial extension or a caudal extension at a distal end thereof. Assuming a number N that is greater than 5, after constraining the anchor members the method includes (i) constraining the anchor members in a collapsed configuration; (ii) positioning a length of locator member 1 behind anchor member 1 and anchor member 2 such that a distal end of locator member 1 extends between anchor member 2 and anchor member 3; (iii) repeating step (ii) for locator members 2, 3, . . . , and N-2; (iv) positioning a length of locator member N-1 behind anchor member N-1 and anchor member N such that a distal end of locator member N-11 extends between anchor member N and anchor member 1; (v) positioning a length of locator member N behind anchor member N and anchor member 1 such that a distal end of locator member N extends between anchor member 1 and anchor member 2; (vi) verifying that the anchor members with caudal extensions are surrounded by the anchor members with cranial extensions; and (vii) pulling the filter into a delivery sheath.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An in vivo vascular blood filter comprising:
  a hub disposed proximally along a longitudinal axis;
  a plurality of anchor members extending from the hub; and
  a plurality of straight, bent, or curved locator members extending from the hub disposed between an adjacent pair of anchor members,
  wherein
  an anchor member comprises a distally disposed cranial extension base or a distally disposed caudal extension base,
  a cranial extension extends from the cranial extension base and comprises a cranial penetration member and a cranial limiter wherein the cranial penetration member comprises a hook portion having a radius of curvature equal to about 0.03 inches and the cranial limiter is straight or curved,
  and a caudal extension extends from the caudal extension base and comprises a caudal penetration member and a caudal limiter.

2. The filter of claim 1 wherein the hook is configured to resist 105 or more g of force when penetrating into vascular tissue.

3. The filter of claim 2 wherein the caudal penetration member is curved.

4. The filter of claim 3 wherein the caudal penetration member has a radius of curvature equal to about 0.3 inches.

5. The filter of claim 4 wherein the caudal limiter has a length greater than or equal to the length of the caudal penetration member.

6. The filter of claim 5 wherein the caudal limiter is straight or curved.

7. An in vivo vascular blood filter comprising:
a hub disposed proximally along a longitudinal axis;
a plurality of anchor members extending from the hub; and
a plurality of straight, bent, or curved locator members extending from the hub disposed between an adjacent pair of anchor members,
wherein
an anchor member comprises a distally disposed cranial extension base or a distally disposed caudal extension base,
a cranial extension extends from the cranial extension base and comprises a cranial penetration member and a cranial limiter,
and
a caudal extension extends from the caudal extension base and comprises a caudal penetration member and a caudal limiter wherein the caudal penetration member is curved and has a radius of curvature equal to about 0.3 inches.

8. The filter of claim 7 wherein the caudal limiter has a length greater than or equal to the length of the caudal penetration member.

9. The filter of claim 8 wherein the caudal limiter is straight or curved.

10. The filter of claim 9 wherein
the cranial penetration member comprises a hook portion, and
the cranial limiter is straight or curved.

11. The filter of claim 10 wherein the hook has a radius of curvature equal to about 0.03 inches.

12. The filter of claim 11 wherein the hook is configured to resist 105 or more g of force when penetrating into vascular tissue.

13. An in vivo vascular blood filter comprising:
a hub disposed proximally along a longitudinal axis;
a plurality of anchor members extending from the hub; and
a plurality of straight, bent, or curved locator members extending from the hub disposed between an adjacent pair of anchor members,
wherein
an anchor member comprises a distally disposed cranial extension base or a distally disposed caudal extension base,
a cranial extension extends from the cranial extension base and comprises:
a cranial penetration member having a hook portion with a radius of curvature equal to about 0.03 inches, configured to resist about 105 or more grams of force when penetrating into vascular tissue; and
a straight or curved cranial limiter,
and
a caudal extension extends from the caudal extension base and comprises:
a curved caudal penetration member with a radius of curvature equal to about 0.3 inches; and
a straight or curved caudal limiter having a length greater than or equal to the length of the caudal penetration member.

\* \* \* \* \*